US009061039B2

(12) United States Patent
Jia et al.

(10) Patent No.: US 9,061,039 B2
(45) Date of Patent: *Jun. 23, 2015

(54) IDENTIFICATION OF FREE-B-RING FLAVONOIDS AS POTENT COX-2 INHIBITORS

(71) Applicant: Unigen, Inc., Seattle, WA (US)

(72) Inventors: Qi Jia, Olympia, WA (US); Timothy C. Nichols, San Diego, CA (US); Eric E. Rhoden, Duluth, GA (US); Scott Waite, Long Beach, CA (US)

(73) Assignee: Unigen, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/970,283

(22) Filed: Aug. 19, 2013

(65) Prior Publication Data

US 2014/0080774 A1    Mar. 20, 2014

Related U.S. Application Data

(63) Continuation of application No. 13/493,820, filed on Jun. 11, 2012, now Pat. No. 8,535,735, which is a continuation of application No. 13/084,419, filed on Apr. 11, 2011, now abandoned, which is a continuation of application No. 11/676,528, filed on Feb. 20, 2007, now Pat. No. 7,972,632, which is a continuation of application No. 10/469,275, filed as application No. PCT/US03/06098 on Feb. 28, 2003, now Pat. No. 7,192,611, which is a continuation of application No. 10/091,362, filed on Mar. 1, 2002, now abandoned.

(51) Int. Cl.
*A01N 65/00* (2009.01)
*A61K 31/7048* (2006.01)
*A61K 36/539* (2006.01)
*A61K 31/353* (2006.01)

(52) U.S. Cl.
CPC ........... *A61K 31/7048* (2013.01); *A61K 36/539* (2013.01); *A61K 31/353* (2013.01)

(58) Field of Classification Search
CPC .................................................. A61K 36/539
USPC ......................................................... 424/725
See application file for complete search history.

(56) References Cited

U.S. PATENT DOCUMENTS

| | | |
|---|---|---|
| 3,686,872 A | 8/1972 | Whitworth et al. |
| 3,706,581 A | 12/1972 | Whitworth et al. |
| 4,035,510 A | 7/1977 | Van Scott et al. |
| 4,268,517 A | 5/1981 | Niebes et al. |
| 4,374,824 A | 2/1983 | Wahmi |
| 4,515,804 A | 5/1985 | Marti et al. |
| 4,627,977 A | 12/1986 | Gaffar et al. |
| 4,946,684 A | 8/1990 | Blank et al. |
| 4,965,067 A | 10/1990 | Wietfeldt |
| 5,037,635 A | 8/1991 | Nabi et al. |
| 5,096,701 A | 3/1992 | White, Jr. et al. |
| 5,098,709 A | 3/1992 | Kang |
| 5,156,835 A | 10/1992 | Nabi et al. |
| 5,437,856 A | 8/1995 | Lukacovic et al. |
| 5,470,589 A | 11/1995 | Shi |
| 5,545,411 A | 8/1996 | Chancellor |
| 5,585,371 A | 12/1996 | Lardy |
| 5,589,160 A | 12/1996 | Rice |
| 5,605,929 A | 2/1997 | Liao et al. |
| 5,643,598 A | 7/1997 | Meybeck |
| 5,650,432 A | 7/1997 | Walker et al. |
| 5,650,433 A | 7/1997 | Watanabe et al. |
| 5,651,987 A | 7/1997 | Fuisz |
| 5,756,538 A | 5/1998 | Cassels et al. |
| 5,766,614 A | 6/1998 | Yong |
| 5,773,014 A | 6/1998 | Perrier et al. |
| 5,795,911 A | 8/1998 | Cheng et al. |
| 5,804,168 A | 9/1998 | Murad |
| 5,852,057 A | 12/1998 | Muto et al. |
| 5,858,371 A | 1/1999 | Singh et al. |
| 5,886,029 A | 3/1999 | Dhaliwal |

(Continued)

FOREIGN PATENT DOCUMENTS

| CA | 2 126 513 A1 | 1/1995 |
|---|---|---|
| CA | 2 451 844 A1 | 1/2003 |

(Continued)

OTHER PUBLICATIONS

"L17—(baicalin near20 catechin) near20 weight" Search History, retrieved Jan. 8, 2009, from http://jupiter1:42900/bin/cgi-bin/PreSearch.p1, 1 page.
"*Scutellaria* Root / *Official Monographs for Part II*," in The Japanese Pharmacopoeia, 14th ed. (English version), Society of Japanese Pharmacopoeia, Tokyo, Japan, 2001, pp. 1042-1043.
Abdulrazak et al., "Chemical Composition, Phenolic Concentration and In Vitro Gas Production Characteristics of Selected *Acacia* Fruits and Leaves," *Asian-Aus J Anim Sci* 13(7):935-940, 2000.
Afolyayan et al., "The antimicrobial activity 3,5,7-trihydroxyflavone isolated from the shoots of *Helichrysum* aureonitens," *Journal of Ethnopharmacol.* 57(3):177-181, 1997.
Agarwal et al., "Protection Against Ultraviolet B Radiation-Induced Effects in the Skin of SKH-1 Hairless Mice by a Polyphenolic Fraction Isolated from Green Tea," *Photochemistry and Photobiology* 58(5):695-700, Nov. 1993.

(Continued)

*Primary Examiner* — Michael Meller
(74) *Attorney, Agent, or Firm* — Seed IP Law Group PLLC

(57) ABSTRACT

The present invention provides a novel method for inhibiting the cyclooxygenase enzyme COX-2. The method is comprised of administering a composition containing a Free-B-Ring flavonoid or a composition containing a mixture of Free-B-Ring flavonoids to a host in need thereof. The present also includes novel methods for the prevention and treatment of COX-2 mediated diseases and conditions. The method for preventing and treating COX-2 mediated diseases and conditions is comprised of administering to a host in need thereof an effective amount of a composition containing a Free-B-Ring flavonoid or a composition containing a mixture of Free-B-Ring flavonoids and a pharmaceutically acceptable carrier.

19 Claims, 8 Drawing Sheets

(56) References Cited

U.S. PATENT DOCUMENTS

| | | |
|---|---|---|
| 5,886,155 A | 3/1999 | Armah et al. |
| 5,908,628 A | 6/1999 | Hou |
| 5,922,756 A | 7/1999 | Chan |
| 5,962,517 A | 10/1999 | Murad |
| 5,968,973 A | 10/1999 | Cheng et al. |
| 6,080,401 A | 6/2000 | Reddy et al. |
| 6,083,921 A | 7/2000 | Xu |
| 6,093,403 A | 7/2000 | Huo et al. |
| 6,113,909 A | 9/2000 | Han et al. |
| 6,126,940 A | 10/2000 | Takahashi et al. |
| 6,126,950 A | 10/2000 | Bindra et al. |
| 6,193,977 B1 | 2/2001 | Han et al. |
| 6,194,469 B1 | 2/2001 | Nair et al. |
| 6,197,808 B1 | 3/2001 | Cheng et al. |
| 6,217,875 B1 | 4/2001 | Murai et al. |
| 6,221,341 B1 | 4/2001 | Montgomery |
| 6,235,294 B1 | 5/2001 | Perrier et al. |
| 6,241,972 B1 | 6/2001 | Herms et al. |
| 6,248,341 B1 | 6/2001 | Anderson et al. |
| 6,264,926 B1 | 7/2001 | Farooqi et al. |
| 6,264,995 B1 | 7/2001 | Newmark et al. |
| 6,280,751 B1 | 8/2001 | Fletcher et al. |
| 6,290,995 B1 | 9/2001 | Xinxian |
| 6,319,523 B1 | 11/2001 | Zhou |
| 6,333,304 B1 | 12/2001 | Bath et al. |
| 6,387,416 B1 | 5/2002 | Newmark et al. |
| 6,391,346 B1 | 5/2002 | Newmark et al. |
| 6,391,872 B1 | 5/2002 | Marfat |
| 6,475,530 B1 | 11/2002 | Kuhrts |
| 6,555,573 B2 | 4/2003 | Rosenbloom |
| 6,576,660 B1 | 6/2003 | Liao et al. |
| 6,685,971 B2 | 2/2004 | Xu |
| 7,045,158 B2 | 5/2006 | Wolfson et al. |
| 7,074,438 B2 | 7/2006 | Xu |
| 7,108,868 B2 | 9/2006 | Jia et al. |
| 7,189,385 B2 | 3/2007 | Montgomery |
| 7,192,611 B2 | 3/2007 | Jia et al. |
| 7,514,469 B2 | 4/2009 | Jia |
| 7,531,521 B2 | 5/2009 | Burnett et al. |
| 7,615,239 B2 | 11/2009 | Santo et al. |
| 7,674,830 B2 | 3/2010 | Jia |
| 7,695,743 B2 | 4/2010 | Jia et al. |
| 7,897,182 B2 | 3/2011 | Woo et al. |
| 7,972,632 B2 | 7/2011 | Jia |
| 8,034,387 B2 | 10/2011 | Jia et al. |
| 8,124,134 B2 | 2/2012 | Jia et al. |
| 8,148,416 B2 | 4/2012 | El-Naggar et al. |
| 8,535,735 B2 | 9/2013 | Jia et al. |
| 2001/0002407 A1 | 5/2001 | Nair et al. |
| 2001/0026813 A1 | 10/2001 | Kim et al. |
| 2001/0046963 A1 | 11/2001 | Wenzel et al. |
| 2002/0086042 A1 | 7/2002 | Delrieu et al. |
| 2002/0086070 A1 | 7/2002 | Kuhrts |
| 2002/0122836 A1 | 9/2002 | Obukowicz et al. |
| 2002/0136784 A1 | 9/2002 | Obukowicz et al. |
| 2002/0146467 A1 | 10/2002 | Jung et al. |
| 2003/0045562 A1 | 3/2003 | El-Naggar et al. |
| 2003/0105030 A1 | 6/2003 | Liao et al. |
| 2003/0113797 A1 | 6/2003 | Jia et al. |
| 2003/0125264 A1 | 7/2003 | Malik |
| 2003/0165588 A1 | 9/2003 | Jia et al. |
| 2003/0166583 A1 | 9/2003 | Yoa-Pu Hu et al. |
| 2003/0170186 A1 | 9/2003 | Geers et al. |
| 2003/0203857 A1 | 10/2003 | Ohnogi et al. |
| 2004/0057908 A1 | 3/2004 | Bowen et al. |
| 2005/0049206 A1 | 3/2005 | Gong et al. |
| 2005/0096281 A1 | 5/2005 | Jia et al. |
| 2007/0264361 A1 | 11/2007 | Jo et al. |
| 2008/0176811 A1 | 7/2008 | Geers et al. |
| 2011/0207806 A1 | 8/2011 | Jia |
| 2011/0245333 A1 | 10/2011 | Jia et al. |
| 2012/0053138 A1 | 3/2012 | Jia et al. |

FOREIGN PATENT DOCUMENTS

| | | |
|---|---|---|
| CN | 1057196 A | 12/1991 |
| CN | 1177492 A | 4/1994 |
| CN | 1093914 A | 10/1994 |
| CN | 1096680 A | 12/1994 |
| CN | 1101856 A | 4/1995 |
| CN | 1189365 A | 8/1998 |
| CN | 1228968 A | 9/1999 |
| CN | 1285202 A | 2/2001 |
| EP | 0 296 625 A2 | 12/1988 |
| EP | 0 633 022 A2 | 6/1994 |
| EP | 0 742 012 A2 | 11/1996 |
| EP | 0 633 022 B1 | 2/1997 |
| EP | 0 956 867 A1 | 11/1999 |
| EP | 1 147 764 A2 | 10/2001 |
| FR | 2 651 132 A | 3/1991 |
| FR | 2 687 572 A | 2/1992 |
| GB | 2 024 817 A | 1/1980 |
| JP | 57-38721 A | 3/1982 |
| JP | 61-050921 A | 3/1986 |
| JP | 61-083179 A | 4/1986 |
| JP | 61-161219 A | 7/1986 |
| JP | 61-233627 A | 10/1986 |
| JP | 61-238719 A | 10/1986 |
| JP | 63-027435 A | 2/1988 |
| JP | 64-90124 A | 4/1989 |
| JP | 3-240725 A | 10/1991 |
| JP | 3-251518 A | 11/1991 |
| JP | 05-271088 A | 10/1993 |
| JP | 05-331061 A | 12/1993 |
| JP | 7-017847 A | 1/1995 |
| JP | 7-25761 A | 1/1995 |
| JP | 07-055895 B | 6/1995 |
| JP | 7-165598 A | 6/1995 |
| JP | 7-223941 A | 8/1995 |
| JP | 7-242555 A | 9/1995 |
| JP | 7-252158 A | 10/1995 |
| JP | 7-277942 A | 10/1995 |
| JP | 8-26969 A | 1/1996 |
| JP | 8-104628 A | 4/1996 |
| JP | 9-94081 A | 4/1997 |
| JP | 09-278662 A | 10/1997 |
| JP | 10-25238 A | 1/1998 |
| JP | 10-182415 A | 7/1998 |
| JP | 10-287528 A | 10/1998 |
| JP | 11-140497 A | 5/1999 |
| JP | 2000-044481 A | 2/2000 |
| JP | 2000-506901 A | 6/2000 |
| JP | 2000-226329 A | 8/2000 |
| JP | 2000-319154 A | 11/2000 |
| JP | 2001-220353 A | 8/2001 |
| JP | 2002-053484 A | 2/2002 |
| JP | 2002-080362 A | 3/2002 |
| JP | 2003-2820 A | 1/2003 |
| JP | 2003-81746 A | 3/2003 |
| JP | 2003-212771 A | 7/2003 |
| JP | 2003-212786 A | 7/2003 |
| JP | 2004-244385 A | 9/2004 |
| KR | 1996-0003725 A | 2/1996 |
| KR | 1996-0040370 A | 12/1996 |
| KR | 2001-0017481 A | 3/2001 |
| KR | 2001-0069130 A | 7/2001 |
| KR | 2002-0013675 A | 2/2002 |
| KR | 2002-0031608 A | 5/2002 |
| KR | 2003-0021640 A | 3/2003 |
| TW | 235922 A | 12/1994 |
| WO | 97/36497 A2 | 10/1997 |
| WO | 98/19651 A1 | 5/1998 |
| WO | 98/40086 A2 | 9/1998 |
| WO | 98/42363 A1 | 10/1998 |
| WO | 98/49256 A1 | 11/1998 |
| WO | 00/59523 A1 | 10/2000 |
| WO | 00/67749 A1 | 11/2000 |
| WO | 00/74662 A2 | 12/2000 |
| WO | 01/30341 A1 | 5/2001 |
| WO | 02/07745 A1 | 1/2002 |
| WO | 02/09699 A2 | 2/2002 |
| WO | 02/39973 A2 | 5/2002 |

(56) References Cited

FOREIGN PATENT DOCUMENTS

| WO | 02/42429 A2 | 5/2002 |
|---|---|---|
| WO | 02/47615 A2 | 6/2002 |
| WO | 03/002134 A1 | 1/2003 |
| WO | 03/009825 A2 | 2/2003 |
| WO | 03/015737 A1 | 2/2003 |
| WO | 03/015766 A1 | 2/2003 |
| WO | 03/024470 A1 | 3/2003 |
| WO | 03/074065 A1 | 9/2003 |
| WO | 03/082312 A1 | 10/2003 |
| WO | 03/092599 A2 | 11/2003 |
| WO | 2004/058279 A1 | 7/2004 |
| WO | 2004/089392 A1 | 10/2004 |
| WO | 2005/020932 A2 | 3/2005 |

OTHER PUBLICATIONS

Amos et al., "The Pharmacological Effects of an Aqueous Extract from *Acacia nilotica* Seeds," *Phytotherapy Research* 13:683-685, 1999.
Ardlie et al., "Effects of Trifluoperazine of Platelet Activation," *Thromb. Res.* 38(6):695-706, 1985.
Asaki et al., "The Effect of Oral Rinses Extracted from Japanese Tea on the Experimental Gingivitis in Man," *Journal of the Japanese Association of Peridontology* 37(2):412-421, 1995. (Abstract only) (3 pages).
Azad et al., "Isolation of (+)-catechin and a new polyphenolic compound in Bengal catechu," *J Wood Sci* 47(5):406-409, 2001.
Babu et al., "Aspirin and Asthma," *Chest* 118:1470-1476, 2000.
Bastianetto et al., "Neuroprotective abilities of resveratrol and other red wine consitituents against nitric oxide-related toxicity in cultured hippocampal neurons," *British Journal of Pharmacology* 131:711-720, 2000.
Baumann et al., "Flavonoids and Related Compounds as Inhibitors of Arachidonic Acid Peroxidation," *Prostaglandins* 20(4):627-639, Oct. 1980.
Bertolini et al., "Dual Acting Anti-Inflammatory Drugs: A Reappraisal," *Pharmacol Res* 44(6):437-450, 2001.
Bhagwat et al., "Flavanoid composition of tea: Comparison of black and green teas," 2003 IFT Annual Meeting and Food Expo, Jul. 12-16, 2003, Chicago, Illinois, 1 page (Poster).
Bhāvamiśra; Bhāvaprakāśa—Edited & translated by Brahmashankara Misra & RupaLalaji Vaisya, Part-I: Chaukhambha Sanskrit Sansthan, Varanasi, Edn. 9$^{th}$, 1999, Time of origin 16$^{th}$ century, p. 110, Formulation ID: RS/3007D, Formulation Name:Dantakūrcikā(04), 3 pages. (with English translation).
Bickford et al., "Antioxidant-rich diets improve cerebellar physiology and motor learning in aged rats," *Brain Res* 866:211-217, Jun. 2, 2000.
Bickford et al., "Effect of Normobaric Hyperoxia on Two Indexes of Synaptic Function in Fisher 344 Rats," *Free Rad Biol Med* 26(7/8):817-824, Apr. 1999.
Bickford et al., "Effects of aging on cerebellar noradrenergic function and motor learning: nutritional interventions," *Mech Ageing Dev* 111:141-154, Nov. 1999.
Boozer et al., "An herbal supplement containing Ma Huang-Guarana for weight loss: a randomized, double-blind trial," *International Journal of Obesity* 25:316-324, 2001.
Bosset et al., "Photoageing shows histological features of chronic skin inflammation without clinical and molecular abnormalities," *Brit J Dermatol* 149:826-835, 2003.
Boumendjel et al., "B-ring substituted 5,7 Dihydroxyflavonols with High-Affinity Binding to P-Glycoprotein Responsible for Cell Multidrug Resistance," *Bioorg. Med. Chem. Lett.* 11(1):75-77, 2001.
Brideau et al., "A Human Whole Blood Assay for Clinical Evaluation of Biochemical Efficacy of Cyclooxygenase Inhibitors,"*Inflamm. Res.* 45:68-74, 1996.
Brock et al., "Arachidonic Acid is Preferentially Metabolized by Cyclooxygenase-2 to Prostacyclin and Prostaglandin $E_2$," *J Biol Chem* 274(17):11660-11666, Apr. 1999.

Bunting et al., "The Prostacyclin-Thromboxane $A_2$, Balance: Pathophysiological and Therapeutic Implications," *Brit Med Bull* 39(3):271-276, 1983.
Butenko et al., "Anti-inflammatory properties and inhibition of leukotriene $C_4$ Biosynthesis in vitro by flavonoid baicalein from *Scutellaria baicalensis* georgy roots," *Agents Actions 39, Special Conference Issue*:C49-C50, 1993.
Butterfield et al., "Structural and Functional Changes in Proteins Induced by Free Radical-mediated Oxidative Stress and Protective Action of the Antioxidants *N-tert*-Butyl-α-phenylnitrone and Vitamin E$^a$, "*Ann NY Acad Sci* 854:448-462, Nov. 20, 1998.
Cao et al., "Hyperoxia-induced changes in antioxidant capacity and the effect of dietary antioxidants," *J Applied Physiol* 86(6):1817-1822, Jun. 1999.
Cao et al., "Oxygen-Radical Absorbance Capacity Assay for Antioxidants," *Free Radical Biology & Medicine* 14:303-311, 1993.
Carney et al., "Reversal of age-related increase in brain protein oxidation, decrease in enzyme activity, and loss in temporal and spatial memory by chronic administration of the spin-trapping compound *N-tert*-butyl-α-phenylnitrone," *Proc. Natl. Acad. Sci. USA* 88:3633-3636, May 1991.
Carson et al., "The cellular response in neuroinflammation: The role of leukocytes, microglia and astrocytes in neuronal death and survival," *Clin Neurosci Res* 6(5):237-245, Dec. 2006.
Cartford et al., "Eighteen-Month-Old Fischer 344 Rats Fed a Spinach-Enriched Diet Show Improved Delay Classical Eyeblink Conditioning and Reduced Expression of Tumor Necrosis Factor α (TNFα) and TNFβ in the Cerebellum," *J Neurosci* 22(14):5813-5816, Jul. 15, 2002.
Caughey et al., "Roles of Cyclooxygenase (COX)-1 and COX-2 in Prostanoid Production by Human Endothelial Cells: Selective Up-Regulation of Prostacyclin Synthesis by COX-2," *J Immunol* 167:2831-2838, 2001.
Celotti et al., "Anti-Inflammatory Drugs: New Multitarget Compounds to Face an Old Problem. The Dual Inhibition Concept," *Pharmacological Research* 43(5):429-436, May 2001.
Chang et al., "Prevention of Lens Protein-Induced Ocular Inflammation with Cyclooxygenase and Lipoxygenase Inhibitors," *J Ocular Pharmacol* 5(4):353-360, 1989.
Chang et al., "Role of 5-Lipoxygenase Products of Arachidonic Acid in Cell-to-Cell Interaction Between Macrophages and Natural Killer Cells in Rat Spleen," *J Leukocyte Biol* 50:273-278, 1991.
Chen et al., "Oroxylin A inhibition of lipopolysaccharide-induced iNOS and COX-2 gene expression via suppression of nuclear factor-kappaB activation," *Biochemical Pharmacology* 59(11):1445-1447, 2000.
Chen et al., "Wogonin, baicalin, and baicalein inhibition of inducible nitric oxide synthase and cyclooxygenase-2 gene expressions induced by nitric oxide synthase inhibitors and lipopolysaccharide," *Biochem. Pharmacol.* 61(11):1417-1427, 2001.
Chi et al., "Effect of wogonin, a plant flavone from *Scutellaria radix*, on the supression of cyclooxygenase-2 and the induction of the inducible nitric oxide synthase in lipopolysaccharide-treated RAW 264.7 cells," *Biochem Pharmacol* 61:1195-1203, May 15, 2001.
Chinese Herbs Direct, retrieved from http://www.chineseherbsdirect.com, 2007, 2 pages.
Chou et al., "The antiinflammatory and Analgesic Effects of Baicalin in Carrageenan-Evoked Thermal Hyperalgesia," *Anesth Analg* 97:1724-1729, 2003.
Christie et al., "Opiods, NSAIDs and 5-lipoxygenase inhibitors act synergistically in brain via arachidonic acid metabolism," *Inflamm Res* 48:1-4, 1999.
Chung et al., "Pharmacological Effects of Methanoloic Extract from the Root of *Scutellaria baicalensis* and its Flavonoids on Human Gingival Fibroblast," *Planta Med.* (*NY*) 61:150-153, 1995.
Clark et al., "Do Some Inhibitors of COX-2 Increase the Risk of Thromboembolic Events?," *Drug Safety* 27(7):427-456, 2004.
Colby, "Calculating Synergistic and Antagonistic Responses of Herbicide Combinations," *Weeds* 15(1):20-22, 1967.
Commenges et al., "Intake of flavonoids and risk of dementia," *Eur. J. Epidemiol* 16:357-363, 2000.

(56) References Cited

OTHER PUBLICATIONS

Dafallah et al., "Investigation of the Ant-inflammatory Activity of *Acacia nilotica* and *Hibiscus sabdariffa*," *American Journal of Chinese Medicine* 24:(3-4):263-269, 1996.
Dannhardt et al., "Cyclooxygenase inhibitors—current status and future prospets," *Eur J Med Chem* 36(2):109-126, Feb. 2001.
Davies et al., "COX-2 selective inhibitors cardiac toxicity: getting to the heart of the matter," *J Pharm Pharmaceut Sci* 7(3):332-336, 2004.
de Gaetano et al., "Prevention of thrombosis and vascular inflammation: benefits and limitations of selective or combined COX-1, COX-2 and 5-LOX inhibitors," *Trends in Pharmacol Sci* 24(5):245-252, May 2003.
de la Puerta et al., "Inhibition of Leukocyte Eicosanoid Generation and Radical Scavenging Activity by Gna phalin, a Lipophilic Flavonol Isolated from *Helichrysum picardii*," *Planta Medica* 65:507-511, 1999.
de Whalley et al., "Flavonoids Inhibit the Oxidative Modification of Low Density Lipoproteins by Machrophages," *Biochemical Pharmacology* 39:1743-1750, 1990.
DeLange et al., "Phycoerythrin Fluorescence-Based Assay for Proxy Radicals: A Screen for Biologically Relevant Protecive Agents," *Analyst Biochem* 177:300-306, 1989.
Dempke et al., "Cyclooxygenase-2: a novel target for cancer chemotherapy?," *J Cancer Res Clin Oncol* 127(7)411-417, Jul. 2001.
Deray, "Renal and cardiovascular effects of non-steroidal anti-inflammatories and selective cox 2 inhibitors,"*Presse Med* 33(7):483-489, Apr. 2004. (with English abstract).
Deshpande et al., "Flavonoids of *Acacia catechu* Heartwood," *Indian Journal of Chemistry* 20B:628, Jul. 1981.
DeWitt, "Cox-2-Selective Inhibitors: The New SuperAspirins," *Mol Pharmacol* 55:625-631, 1999.
Elattar et al., "Hydoxy fatty acids and prostaglandin formation in diseased human periodontal pocket tissue," *Journal of Periodontal Research* 21:169-176, 1986.
Engler et al., "The vasculoprotective effects of flavonoid-rich cocoa and chocolate," *Nutrition Res* 24:695-706, 2004.
Exotic Naturals, "*Acacia* Catechu Extract," retrieved Apr. 19, 2007 from, www.exoticnatural.com/acacia-catechu.htm, 2 pages.
Fenton et al., "Characterization of the Effects of Antiangiogenic Agents on Tumor Pathophysiology," *Am J Clin Oncol (CCT)* 24(5):453-457, 2001.
Fiorucci et al., "Dual inhibitors of cyclooxygenase and 5-lipoxygenase. A new avenue in anti-flammatory therapy?, " *Biochem Pharmacol* 62:1433-1438, 2001.
Fogh et al., "Modulation of Eicosanoid Formation by Lesional Skin of Psoriasis: An Ex vivo Skin Model," *Acta Derm Venerol (Stockh)* 73:191-193, 1993.
Friedman et al., "NSAIDs in Dermatologic Therapy: Review and Preview," *J Cutan Med Surg* 6(5):449-459, 2002.
Gabrielska et al., "Antioxidant Activity of Flavones from *Scutellaria baicalensis* in Lecithin Liposomes," *Verlag der Zeitschrift für Naturforschung*, pp. 817-823, 1997.
Gaffar et al., "The effect of triclosan on mediators of gingival inflammation," *J Clin Periodontal* 22:480-484, 1995.
Gafner et al., "Evaluation of the anti-inflammatory properties of skullcap (*Scutellaria laterifora* L.) extracts in different in vitro models," 2004 International Congress on Natural Products Research, Phoenix, Arizona, Jul. 31-Aug. 4, 2004, P:60 and poster. (3 pages).
Gemma et al., "Diets Enriched in Foods with High Antioxiant Activity Reverse Age-Induced Decreases in Cerebellar β-Adrenergic Function and Increases in Proinflammatory Cytokines," *J Neurosci* 22(4):6114-6120, Jul. 15, 2002.
Gilani et al., "Studies on Antihypertensive and Antispasmodic Activities of Methanol Extract of *Acacia nilotica* Pods," *Phytotherapy Res* 13(8):665-669, Dec. 1999.
Gilroy et al., "Inducible cyclooxygenase may have anti-inflammatory properties," *Nature Med* 5(6):698-701, Jun. 1999.
Giovannucci et al., "Aspirin and the Risk of Colorectal Cancer in Women," *N Engl J Med* 333(10):60-614, Sep. 7, 1995.
Goebel et al., "Procainamide, a Drug Causing Lupus, Induces Prostaglandin H Synthase-2 and Formation of T Cell-Sensitizing Drug Metabolites in Mouse Macrophages," *Chem Res Toxicol* 12(6):488-500, 1999.
Gök et al., "Role of Leukotrienes on Coronary Vasoconstriction in Isolated Hearts of Arthritic Rats: Effect of in vivo Treatment with CI-986, a Dual Inhibitor of Cyclooxygenase and Lipoxygenase," *Pharmacol* 60:41-46, 2000.
Gould et al., "Antioxidant protection of cerebellar β-adrenergic receptor function in aged F344 rats," *Neurosci Lett* 250:165-168, Jul. 10, 1998.
Greenspan et al., "Carboxy-Substituted Cinnamides: A Novel Series of Potent, Orally Active $LTB_4$ Receptor Antagonists," *J Med Chem* 42(1): 164-172,1999.
Gupta, V. K., Senior Advisor and Director, TKDL, Third Party Observations, dated Sep. 10, 2010, in Canadian Application No. 2,584,124; received in CIPO Sep. 30, 2010, 7 pages.
Gupta, V. K., Senior Advisor and Director, TKDL, Third Party Observation, dated Feb. 7, 2011 in Canadian Application No. 2,521,429; received in CIPO Feb. 15, 2011, 8 pages.
Gupta, V. K., Senior Advisor and Director, TKDL, Third Party Observation, dated Apr. 26, 2011, in European Application No. 05810437.3; received in EPO May 9, 2011, 7 pages.
Hagos et al., "Isolation of Smooth Muscle Relaxing 1,3-Diarylpropan-2-ol Derivatives from *Acacia tortilis*," *Planta Med* 53(1):27-31, Feb. 1987.
Hamazaki et al., "Catechin's activitiy of inhibiting LTC4 production," *Allergy* 49(9/10):914, 2000, 2 pages. (with English translation).
Hanausek-Walaszek et al., Inhibitory Effects of Triterpenoid Saponins From *Acacia victoriae* on Dimethylbenz [A] Anthracene-Induced Murine Skin Carcinogenesis, Proceedings American Association for Cancer Research Annual Meeting 41:663 (Abstract #4216), Mar. 2000.
Haridas et al., "Avicins: Novel Triterpenoid Saponins from *Acacia victoriae*(Benth) Induce Apoptosis by Mitochondrial Perturbation," *Proceedings American Association for Cancer Research Annual Meeting* 41:600 (Abstract #3820), Mar. 2000.
Harrington et al., "Antithrombotic Therapy for Coronary Artery Disease: The Seventh ACCP Conference on Antithrombotic and Thrombolytic Therapy," *Chest* 126 (3 Suppl):513S-548S, Sep. 2004.
Hase et al., "Histological increase in inflammatory infiltrate in sun-exposed skin of female subjects: the possible involvement of matrix metalloproteinase-1 produced by inflammatory infiltrate on collagen degradation," *Br J Dermatol* 142(2):267-273, 2000.
Hennekens, "Update on Aspirin in the Treatment and Prevention of Cardiovascular Disease," *Am J Manag Care* 8(22 Suppl):S691-S700, Dec. 2002.
Heo et al., "Anti-genotoxicity of galangin as a cancer chemopreventive agent candidate," *Mutat. Res.* 488(2):135-150, 2001.
Heo et al., "Potent Inhibitory Effect of Flavonoids in *Scutellaria baicalensis* on Amyloid β Protein-Induced Neurotoxicity," *Journal of Agricultural and Food Chemistry* 52(13):4128-4132, Jun. 30, 2004. (Abstract only).
Herschman, "Regulation of prostaglandin synthase-1 and prostaglandin synthase-2," *Cancer Metastasis Rev* 13(3-4):241-256, Dec. 1994.
Hiipakka et al., "Structure-activity relationships for inhibition human 5α-reductases by polyphenols," *Biochem Pharmacol* 63:1165-1176, 2002.
Hiraoka, "Long-Term Efficacy of COX-2 Selective Inhibitor Etodolac (Hypen®) on Chronic Low Back Pain and/or Osteoarthritis," *Clin Med* 16(7):1037(107)-1045(115), Jul. 2000, 18 pages. (English translation provided).
Ho et al., "Neuronal Cyclooxygenase 2 Expression in the Hippocampal Formation as a Function of the Clinical Progression of Alzheimer Disease," *Arch Neurol* 58:487-492, Mar. 2001.
Hong et al., "Effects of purified green and black tea polyphenols on cyclooxygenase-and lipoxygenase-dependent metabolism of arachidonic acid in human colon mucosa and colon tumor tissues," *Biochemical Pharmacology* 62:1175-1183, 2001.
Hukkeri et al., "Anti-Inflammatory Activity of Leaves of *Acacia farnesiana* Wild," *Indian Drugs* 39(12):664-666, Dec. 1, 2002.

(56) References Cited

OTHER PUBLICATIONS

Imamura et al., "Inhibitory Effects of Flavonoids on Rabbit Heart Carbonyl Reductase," *J. Biochem.* 127(4):653-658, 2000.
*Indian Herbal Pharmacopoeia* (Revised New Edition 2002), Indian Drug Manufacturers' Association, Mumbai, India, 2002, pp. 1-11.
Itoigawa et al., "Structure-activity relationship of cardiotonic flavonoids in guinea-pig papillary muscle," *J. Ethnopharmacol.* 65(3):267-272, 1999.
Itou et al., "Compsns. acting on dental caries and periodontosis—contain polyphenol cpds. pref. obtd. from tea by extn. with water," WPI/Thomson Database, Accession No. 1989-147372 [20], 1989, 1 page.
Jaeckel et al., "Correlation of Expression of Cyclooxygenase-2, Vascular Endothelial Growth Factor, and Peroxisome Proliferator-Activated Receptor δ With Head and Neck Squamous Cell Carcinoma," *Arch Otolaryngol Head Neck Surg* 127(10): 1253-1259, Oct. 2001.
Jia et al., "Identification of free-B-ring flavonoids as potent cyclooxygenase 2 (COX-2) inhibitors," Derwent Abstract of U.S. Patent Application No. 2003-165588 A1, Accession No. 139:191432 CA, 1 page.
Jüni et al., "Risk of cardiovascular events and rofecoxib: cumulative meta-analysis," *Lancet* 364:2021-2029, Dec. 2004.
Kakegawa et al., "Inhibitory Effects of Tannins on Hyaluronidase Activation and on the Degranulation from Rat Mesentery Mast Cells," *Chem. Pharm Bull.* 33(11):5079-5082, 1985.
Kalkbrenner et al., "In vitro Inhibition and Stimulation of Purified Prostaglandin Endoperoxide Synthase by Flavonoids: Structure-Activity Relationship," *Pharmacology* 44(1);1-12, 1992.
Kaneko et al., "Protective Effect of Flavonoids on Endothelial Cells Against Linoleic Acid Hydroperoxide-induced Toxicity," *Biosci. Biotechnol. Biochem.* 63(2):323-328, 1999.
Kang et al., "Antithrombotic Activities of Green Tea Catechins and (−)-Epigallocatechin Gallate," *Thrombosis Research* 96(3)229-237, Nov. 1, 1999. (Abstract only).
Kao et al., "Modulation of Endocrine Systems and Food Intake by Green Tea Epigallocatechin Gallate," *Endocrinol* 141(3):980-987, 2000.
Kawasaki et al., "In Vitro Antiallergic Activity of Flavonoids in Histamine Release Assay Using Rat Basophilic Leukemia (RBL-2H3) Cells," *Journal* of the Food Hygienic Society of *Japan* 33(5): 497-503, Oct. 1994.
Khan, Mohammad Akmal, Qaraabaadeen Azam wa Akmal (20th century AD), Matba Siddiqi, Delhi/Matba Mustafai, Delhi, 1909 AD, p. 173; Formulation ID:BA3/1032; Formulation Name; Nuskha Sanoon. (3 pages) (with English Translation).
Khan, Mohammad Akmal, Qaraabaadeen Azam wa Akmal (20th century AD), Matba Siddiqi, Delhi/Matba Mustafai, Delhi, 1909 AD p. 354, Formulation ID: AH5/199A, Formulation Name: Tila Fasaade-Laun, 2 pages. (with English translation).
Khan, Mohammad Akmal, Qaraabaadeen Azam wa Akmal (20th century AD), Matba Siddiqi, Delhi/Matba Mustafai, Delhi, 1909 AD p. 410, Formulation ID:AH5/610, Formulation Name: Sanoon Bara e-Zirs, 3 pages. (with English translation).
Khan, Mohammad Azam; Muheet-e-Azam, vol. III (19th century AD), Matba Nizami, Kanpur, 1887 AD, p. 37, Formulation ID:JA7/36D, Formulation Name: Tila Bara-e Asaraat-e-Harq, 2 pages. (with English translation).
Khan, Mohammad Najmul Ghani; Qaraabaadeen Najm-al-Ghani (20th century AD), Munshi Nawal Kishore, Lucknow, (Second Edition), 1928 AD p. 667, Formulation ID: NA 4/4357, Formulation Name: Raughan, 4 pages. (with English translation).
Kikukawa et al., "Mechanism of suppressive action of TJ114 upon murine type II collagen-induced arthritis,"*Ensho* 15(2):129-133, 1995. (abstract only).
Kim et al., "Pharmacological Activates of Flavonoids (I)—Relationships of Chemical Structure of Flavonoids and their Inhibitory Activity of Hypersensitivities,"*Yakhak Hoeji* 34(5); 348-364, 1990.
Kimura et al., "Effects of Baicalein Isolated from *Scutellaria baicalensis* Radix on Adhesion Molecule Expression Induced by Thrombin and Thrombin Receptor Agonist Peptide in Cultured Human Umbilical Vein Endothelial Cells,"*Planta Med.* 67:331-334, 2001.
Kirchner et al., "Effects of tepoxalin, a dual inhibitor of cyclooxygenase/5-lipoxygenase, on events associated with NSAID-induced gastrointestinal inflammation,"*Prostaglandins, Leukotrienes and Essential Fatty Acids* 56(6):417-423, Jun. 1997.
Kirschenbaum et al., "The Role of Cyclooxygenase-2 in Prostate Cancer,"*Urology* 58(Suppl 2A):127-131, Aug. 2001.
Klickstein et al., "Lipoxygenation of Arachidonic Acid as a Source of Polymorphonuclear Leukocyte Chemotactic Factors in Synovial Fluid and Tissue in Rheumatoid Arthritis and Spondyloarthritis,"*J Clin Invest* 66(5):1166-1170, Nov. 1980.
Koga et al., "Effect of plasma metabolites of (+)-catechin and quercetin on monocyte adhesion to human aortic endothelial cells,"*Am J Clin Nutr* 73:941-948, 2001.
Kong, "Aspirin in Cardiovascular Disorders—What is Optimum Dose?,"*Am J Cardiovasc Drugs* 4(3):151-158, 2004.
Krakauer et al., "The flavonoid baicalin inhibits superantigen induced inflammatory cytokines and chemokines,"*FEBS Lett.* 500:52-55, 2001.
Kubo et al., "Flavonols from *Heterotheca* inuloides: Tyrosinase Inhibitory Activity and Structural Criteria,"*Bioorg. Med. Chem.* 8(7):1749-1755, 2000.
Kubo et al., "Studies on Scutellariae Radix. Part II: The Antibacterial Substance,"*Journal of Medicinal Plant Research* 43:194-201, 1981.
Kubo et al., "Studies on Scutellariae Radix. VII. Anti-arthritic and Anti-inflammatory Actions of Methanolic Extract and Flavonoid Components from Scutellariae Radix,"*Chem. Pharm. Bull.* 32(7):2724-2729, 1984.
Kuhn et al., "Action of cyclooxygenase (COX) and lipoxygenase (LOX) inhibitors as well as of oxygen free radical scavengers (OFRS) in vasodepression," *Biomed Biochim Acta* 47(10/11):S320-S323, 1998.
Kulkarni et al., "Licofelone—A Novel analgesic and Anti-Inflammatory Agent," *Current Topics Med Chem* 7(3):251-263, 2007.
Kuppusamy et al., "Effects of Flavonoids on Cyclic Amp Phosphodiesterase and Lipid Mobilization in Rat Adipocytes," *Biochem Pharmacol* 44(7):1307-1315, 1992.
Kuppusamy et al., "Potentiation of β-Adrenoceptor Agonist-Mediated Lipolysis by Quercetin and Fisetin in Isolated Rat Adipocytes," *Biochem Pharmacol* 47(3):521-529, 1994.
Lamarque, "Safety of the selective inhibitors the inducible cyclooxygenase-2 take for long period," *Bull Cancer* 91:S117-S124, 2004.
Laughton et al., "Inhibition of Mammalian 5-Lipoxygenase and Cyclo-Oxygenase by Flavonoids and Phenolic Dietary Additives," *Biochem Pharmacol* 42(9): 1673-1681, 1991.
Lee et al., "Antitumor Agents. 49.1 Tricin,Kaempferol-3-0-β-D-Glucopyranoside and (+)-Nortrachelogenin, Antileukemic Principles from *Wikstroemia indicia," J Nat Prod* 44:530-535, Sep.-Oct. 1981.
Lee et al., "Inhibition of oxidative DNA dama, 8-OHdG, and carbonyl contents in smokers treated with antioxidants (vitamin E, vitamin C, β-carotene and red ginseng)," *Cancer Lett* 132:219-227, 1998.
Lee et al., "Pharmacokinetics of Tea Catechins after Ingestion of Green Tea and (—)-Epigallocatechin-3-gallate by Humans: Formation of Different Metabolites and Individual Variability," *Cancer Epidemiol, Biomarkers & Prev 11*: 1025-1032, Oct. 2002.
Lee et al., "Salicylic Acid peels for the Treatment of Acne Vulgaris in Asian Patients," *Dermatol Surg* 29(12):1196-1199, 2003.
Lenton et al., "Ability of human plasma to protect against ionizing radiation is inversely correlated with age," *Mech Ageing Dev* 107:15-20, Feb. 1, 1999.
Levy et al., "Safety and efficacy of flavocoxid compared with naproxen in subjects with osteoarthritis of the knee: a pilot study," *ICRS 2007*, 5 pages.
Leyden, "A review of the use of combination therapies for the treatment of acne vulgaris," *J Am Acad Dermatol* 49(3 Suppl):S200-S210, 2003. (Abstract only).
Leyden, "Guest Editorial," *J Am Acad Dermatol* 49(3 Suppl.):S199, 2003.

(56) References Cited

OTHER PUBLICATIONS

Li et al., "Chemoprevention of 7,12-dimethylbenz[a]anthracene (DMBA)-induced oral carcinogenesis in hamster cheek pouch by a cyclooxygenase 2 inhibitor (Celecoxib) and a 5-lipoxygenase inhibitor (Zileuton)," *AACR Meeting Abstracts*, Abstract No. 546-a, 2004. (1 page).

Li et al., "The flavonoid baicalin exhibits anti-inflammatory activity by binding to chemokines," *Immunopharmacology* 49:295-306, 2000.

Li et al., "The effect of Radix Scutellariae on butyrate of Porphyromonas endodantalis in vitro," *West China J. Stomatol.* 22(1):57-61, 2004, 1 page. (Abstract Only).

Liang et al., "Suppression of inducible cyclooxygenase and nitric oxide synthase through activation of peroxisome proliferator-activated receptor-γ by flavonoids in mouse macrophages," *FEBS Lett.* 496(1):12-18, 2001.

Liao et al., "Selective Inhibition of Steroid 5α-Reductase Isozymes by Tea Epicatechin-3-Gallate and Epigallaocatechin-3-Gallate," *Biochem Biophys Res Comm* 214(3):833-838, 1995.

Lynch, "Age-Related Impairment in Long-Term Potentiation in Hippocampus: A Role for the Cytokine, Interleukin-1β?," *Prog Neurobiol* 56:571-589, Dec. 1998.

Majoosi, Ali Lbn-e-Abbaas, Kaamil-al-Sena'ah, Part II (10$^{th}$ century AD), Central Council for Research in Unani Medicine, 61-85 Institutional Area, Janak Puri, New Delhi-58, 2005, p. 129; Formulation ID:AH3/876C; Formulation Name:Zimaad Baraae Qooba, 3 pages. (with English Translation).

Martel-Pelletier et al., "Therapeutic role of dual inhibitors of 5-LOX and COX, selective and non-selective non-steroidal anti-inflammatory drugs," *Ann. Rheum. Dis.* 62:501-509, 2003.

Mayo Clinic, "Alzheimer's disease," Feb. 10, 2009, 2 pages.

McAdam et al., "Systemic biosynthesis of prostacyclin by cyclooxygenase (COX)-2: The human pharmacology of a selective inhibitor of COX-2," *Proc. Natl. Acad. Sci. USA* 96:272-277, Jan. 1999.

MedicineNet.com "Rheumatoid Arthritis (RA)," Retrieved on Jun. 4, 2009 from, www.medicinenet.com/rheumatiod_arthritis/article.htm, 4 pages.

Meyer et al., "Antiviral of galangin isolated from the aerial parts of *Helichrysum aureonitens*," *J. Ethnopharmacol.* 56(2):165-169, 1997.

Millikan, "The Rationale for Using a Topical Retinoid for Inflammatory Acne," *Am J Clin Dermatol* 4(2):75-80, 2003.

Min et al., "(−)-Epiafzelechin: Cyclooxygenase-1 Inhibitor and Anti-Inflammatory Agent from Aerial Parts of *Celastrus orbiculatus*," *Planta Med.* 65:460-462, 1999.

Miyamoto et al., "Studies on selection method of crude drugs by statistical analysis. Research on Rhubarb having anti-inflammatory activity," *Natural Medicine* 55(4):159-164, 2001. (with English abstract).

Montine et al., "Antioxidants significantly affect the formation of different classes of isoprostanes and neuroprostanes in rat cerebral synaptosomes," *Biochem Pharmacol* 65(4):611-617, Feb. 15, 2003.

Moore et al., "COX-2 Inhibition, Apoptosis, and Chemoprevention by Nonsteroidal Anti-inflammatory Drugs," *Curr Med Chem* 7(11):1131-1144, 2000.

Morimoto et al., "Effects of *Bofu-tsusho-san*, a traditional Chinese medicine on body fat accumulation in fructose-loaded rats," *Nippon Yakurigaky Zasshi* 117:77-86, 2001. (English Abstract provided).

Moroney et al., "Selectivity of Neutrophil 5-Liposygenase and Cyclo-oxygenase Inhibition by an Anti-Inflammatory Flavonoid Glycoside and Related Aglycone Flavonoids," *J. Pharm. Pharmacol.* 40:787-792, 1988.

Murari et al., "A Study of the Components of Cutch: Isolation of Catechin, Gallocatechin, Dicatechin Tetramer as Methyl Ethers," *Indian Journal of Chemistry* 14B(9):661-664, 1976.

Murase et al., "Beneficial effects of tea catechins on diet-induced obesity: stimulation of lipid catabolism in the liver," *International Journal of Obesity* 26:1459-1464, 2002.

Murray et al., "Dietary Supplementation with Vitamin E Reverses the Age-related Deficit in Long Term Potentiation in Dentate Gyrus," *J Biol Chem* 273(20):12161-12168, May 15, 1998.

Mutoh et al., "Suppression by Flavonoids of Cyclooxygenase-2 Promoter-dependent Transcriptional Activity in Colon Cancer Cells: Structure-Activity Relationship," *Jnp. J. Cancer Res.* 91:686-691, 2000.

Nadkarni, A. K., ed., Dr. K. M. Nadkarni's Indian Materia Medica: With Ayurvedic, Unani-Tibbi, Siddha, Allopathic, Homeopathic, Naturopathic & Home Remedies, Appendices & Indexes: vol. 1, Popular Prakashan Pvt. Ltd., Bombay, 1976, pp. 8-17. (7 pages).

Nagai et al., "Inhibition of Mouse Liver Sialidase by the Root of *Scutellaria baicalensis*," *Planta Medica* 55:27-29, 1989.

Nakagami (Aug. 22, 1995) abstract Database WPI Week 199519 Aug. 22. 1995, Derwent Publications Ltd., London, GB; Class 954, p. 2, AN 1995-325471 XP002418722 "Anti-complementary substance used as therapeutic agent—comprises gallic acid, methyl gallate, acetyl-salicyclic acid, caffeic acid, catechin, epi-gallo-catechin gallate, myricetin, quercitrin and/or baicalein, or their salts," & JP07 223941 A ((NIHA-N) Nippon Ham KK).

Nakahata, N., et al., "Analysis of Inhibitory Effects of Scutellariae Radix and Baicalein on Prostaglandin E2 Production in Rat C6 Glioma Cells," *Am. J. Chin. Med.* 26(3-4):311-323, 1998.

Nakahata et al., "Inhibition of Mitogen-activated protein kinase cascade by baicalein, a flavonoid of natural origin," *Nippon Yakurigaku Zasshi (Folia Pharmacol. Jpn.)* 114 (*Supp. 1*):215P-219P, 1999. (with English Abstract).

Nakajima et al., "Inhibitory Effect of Baicalein, a Flavonoid in *Scutellaria* Root, on Eotaxin Production by Human Dermal Fibroblasts," *Planta Med.* 67(2):132-135, 2001.

Nakamura et al., "Arachidonic Acid Cascade Inhibitors Modulate Phorbol Ester-Induced Oxidative Stress in Female ICR Mouse Skin; Differential Roles of 5-Lipoxygenase and Cyclooxygenase-2 in Leukocyte Infiltration and Activation," *Free Radical Biol Med* 35(9):997-1007, Aug. 2003.

Nishioka et al., "Baicalein, an α-Glycosidase Inhibitor from *Scutellaria baicalensis*," *Journal of Natural Products* 61:1413-1415, 1998.

Nityanāthasiddhah; Rasaratnākarah-Rasendra khandam Comm. Datto Vallāl Borakara, Ed. 2$^{nd}$, 1986, Shri Gajānan Book Depot, (Pune), p. 756, Formulation ID:RJ/30, Formulation Name: Kusthaharalepah (02), 3 pages. (with English translation).

Niwa et al., "Application of New Drugs to the Elderly (12)—COX-2 Selective Inhibitor," *Geriatric Gastroenterology* 10(3):181-184, 1998. (with English Translation) (9 pages).

Noreen et al., "Development of a Radiochemical Cyclooxygenase-1 and -2 in Vitro Assay for Identification of Natural Products as Inhibitors of Prostaglandidn Biosynthesis," *Journal of Natural Products* 61:2-7, Jan. 1998.

Noreen et al., "Flavan-3-ols Isolated From Some Medicinal Plants Inhibiting COX-1 and COX-2 Catalyzed Prostaglandin Biosynthesis," *Planta Medica* 64:520-524, 1998.

Noreen et al., "Two New Isoflavones from *Ceiba pentandra* and Their Effect on Cyclooxygenase-Catalyzed Prostaglandin Biosynthesis," *Journal of Natural Products* 61:8-12, Jan. 1998.

Nutracon 2008 NutriAward, retrieved May 1, 2008, from http://www.nutraconference.com/nutraward.index.cfm, 2 pages.

Oringer, "Modulation of the Host Response in Periodontal Therapy," *J Periodontal* 73(4):460-470, Apr. 2002.

Parente, "Pros and Cons of Selective Inhibition of Cyclooxygenase-2 versus Dual Lipoxygenase/Cyclooxygenase Inhibition: Is Two Better than One?," *J Rheumatol* 28:2375-2382, Nov. 2001.

Park et al., "Involvement of ERK and Protein Tyrosine Phosphatase Signaling Pathways in EGCG-Induced Cyclooxygenase-2 Expression in Raw 264.7 Cells," *Biochemical and Biophysical Research Communications* 286:721-725, 2001.

Patrono et al., "Functional Significance of Renal Prostacyclin and Thromboxane $A_2$ Production in Patients with Systemic Lupus Erythematosus," *J Clin Invest* 76:1011-1018, 1985.

Patrono et al., "Drug Therapy: Low-Dose Aspirin for the Prevention of Atherothrombosis," *N. Engl. J. Med.* 353(22), 2005, 18 pages.

Phillips et al., "Polarized light photography enhances visualization of inflammatory lesions of acne vulgaris," *J Am Acad Dermatol* 37(6):948-952, 1997.

(56) References Cited

OTHER PUBLICATIONS

Rae et al., "Leukotriene B$_4$, An Inflammatory Mediator in Gout," *Lancet 320*(8308):1122-1124, Nov. 1982.
Rainsford, "The ever-emerging anti-inflammatories. Have there been any real advances?," *J Physiol—Paris 95*:11-19, 2001.
Ramesiiwaii et al., "Chemical Constituents of *Acacia*," 1997, 2 pages.
Raso et al., "Inhibition of inducible nitric oxide synthase and cyclooxygenase-2 expression by flavonoids in microphage J774A," *Life Sci. 68*(8):921-931, 2001.
Raz et al., "Differential modification of cyclo-oxygenase and peroxidase activities of prostaglandin endoperoxidase synthase by proteolytic digestion and hydroperoxides," *Biochem J 269*(3):603-607, 1990.
Raz et al., "Regulation of Fibroblast cyclooxygenase Synthesis by Interleukin-1," *J Biol Chem 263*(6):3022-3028, Feb. 25, 1988.
Reinhard, "*Uncaria tomentosa* (Willd.) D.C.: Cat's Claw, Uña de Gato, Savéntaro," *The Journal of Alternative and Complementary Medicine 5*(2):143-151, 1999.
Rioja et al., "An anti-inflammatory ditriazine inhibitin leukocyte functions and expression of inducible nitric oxide synthase and cyclo-oxygenase-2," *Eur J Pharmacol 397*(1):207-217, May 2000.
RÖMPP Encyclopedia Natural Products, W. Steglich, B. Fugmann, and S. Lang-Fugmann, Eds., "Tanning Agents," p. 630, Georg Thieme Verlag, Stuttgart, Germany, 2000, 3 pages.
Saleem et al., "Chemistry of the Medicinial Plants of Genus *Acacia*," *Hamdard Medicus 41*(1):63-67, 1998.
Salmon et al., "Evaluation of Inhibitors of Eicosanoid Synthesis in leukocytes: Possible Pitfall of Usinig the Calcium Ionophore A23187 to Stimulate 5' Lipoxygenase," *Prostaglandins 29*(3):377-385, 1985.
Sánchez-Borges et al., "NSAID Hypersensitivity in the COX-2 Inhibitor Era," *ACI International 13*:211-218, 2001.
Sartor et al., "Inhibition of matrix-proteases by polyphenols: chemical insights for anti-inflammatory and anti-invasion drug design," *Biochem Pharmacol 64*:229-237, 2002.
Sekine et al., "Structure and Synthesis of a New Monoterpenoidal Carboxamide from the Seeds of the Thai Medicinal Plant *Acacia concinna*," *Chemistry and Pharmaceutical Bulletin 45*(1):148-151, 1997.
Shah et al., "The Antiplatelet Aggregatory Activity of *Acacia nilotica* is Due to Blockade of Calcium Influx through Membrane Calcium Channels," *General Pharmacology 29*(2):251-255, 1997.
Sharma, "Chemical Constituents of *Acacia* catechu Leaves," *J Indian Chem Soc 74*Jan. 1997, 1 page.
Sharon et al., "Production of Leukotrienes by Colonic Mucosa from Patients with Inflammatory Bowel Disease (IBD)," *Gastroenterology 84*(5), 1983, 1 page.
Shen, "Inhibition of thrombin: relevance to anti-thrombosis strategy," *Frontiers Biosci 11*:113-120, Jan. 2006.
Shibata et al., "Pharmacological Study of Kumazasa (Report 1) Acute toxicity, anti-inflammatory and antiulcerative effects of kumazasa water soluble fraction (Folin)," *Folia pharmacol Japan 71*(5): 481-490, 1975. (with English Abstract).
Smalley et al., "Use of Nonsteroidal Anti-inflammatory Drugs and Incidence of Colorectal Cancer," *Arch Intern Med 159*(2):161-166, Jan. 25, 1999.
So et al., "Inhibition of proliferation of estrogen receptor-positive MCF-7 human breast cancer cells by flavonoids in the presence and absence of excess estrogen," *Cancer Lett.112*(2):127-133, 1997.
Sobottka et al., "Effect of Flavonol Derivatives on the Carrageenin-Induced Paw Edema in the Rat and Inhibition of Cyclooxygenase-1 and 5-Lipoxygenase in Vitro," *Arch. Pharm. Pharm. Med. Chem. 333*:205-210, 2000.
Sodhala; Gadanigrahah ed, Ganga Sahayah Pandeya & Com., Indradeva Tripathi, Part-1 (Prayoga Khanda) Chaukhamba Sanskrit Sansthan, Varanasi, Ed. 3$^{rd}$ 1999, p. 107-108, Formulation ID:AK2/158, Formulation Name: Khadiradyam Tailam, 6 pages. (with English translation).
Sodhala; Gadanigrahah ed, Ganga Sahayah Pandeya & Com., Indradeva Tripathi, Part-3 (Salakya-Pancakarma Khanda) Chaukhamba Sanskrit Sansthan (Varanasi) Ed. 3$^{rd}$ 1999, p. 225, Formulation ID: RG2/525, Formulation Name: Dantasula Cikitsa, 3 pages. (with English Translation).
Stadtman et al., "Reactive Oxygen-Mediated Protein Oxidation in Aging and Disease," *Drug Metab Rev 30*:225-243, May 1998.
Stanke-Labesque et al., "Angiotensin II-induced contractions in human internal mammary artery:effects of cyclooxygenase and lipoxygenase inhibition," *Cardiovasc Res 47*376-383, 2000.
Takada, "Catechin-containing soap includes tea-originated catechin as one of green tea ingredients," WPI/Thomson Database, Accession No. 1999-367373 [31], Oct. 31, 1997, 1 page.
Tanaka, "Cosmetics for preventing agin of skin, comprises elastase inhibitor such as catechin, flavones, flavonols, flavanone, isoflavanones, coumarin and/or their glycosides" WPI/Thomson Database, Accession No. 2003-451711 [43], & JP 2003002820A, Jan. 8, 2003, 4 pages.
Tordera et al., "Influence of Anti-Inflammatory Flavonoids on Degranulation and Arachidnoic Acid Release in Rat Neutrophils," *Z. Naturforsch [c] 49*:235-240, 1994.
Tsao et al., "Effect of Chinese and Western Antimicrobial Agents on Selected Oral Bacteria," *Journal of Dental Research 61*(9):1103-1106, 1982.
Vāgbhata; Astānga Samgraha—(commentary by Indu), Part-I(KA); Central Council for Research in Ayurveda & Siddha, New Delhi, 1991, Time of origin 5-10$^{th}$ century, p. 27, Formulation ID: AT/2103, Formulation Name: Gandūsadhāranādigunaāh, 3 pages. (with English Translation).
Vautrin, "Etude botanique chimique et pharmacologique du genre *Acacia*. (Botanical, chemical and pharmacological study of the *Acacia* species).," Universitie de Dijon (France) 94 pp., 1996, Abstract #58/646c in *Dissertation Abstracts International 58*(1):177-C, 1997.
Wakabayashi et al., "Wogonin inhibits inducible prostaglandin E2 production in macrophages," *Eur. J. Pharmacol. 406*(3):477-448, 2000.
Wallace et al., "Limited anti-inflammatory efficacy of cyclo-oxygenase-2 inhibition in carrageenan-airpouch inflammation," *Br J Pharmacol 126*:1200-1204, 1999.
Wang, "Cyclooxygenase active bioflavonoids from Balaton™ tart cherry and their structure activity relationships," *Phytomedicine 7*:15-19, 2000.
Weinberg, "Nitric Oxide Synthase 2 and Cyclooxygenase 2 Interactions in Inflammation," *Immunol Res 22*(2-3):319-341, 2000.
Wenzel et al., "Dietary Flavone is a Potent Apoptosis Inducer in Human Colon Carcinoma Cells," *Cancer Res. 60*3823-3831, 2000.
Whelton et al., "Cyclooxygenase-2 Specific Inhibitors and Cardiorenal Function: A Randomized, Controlled Trial of Celecoxib and Rofecoxib in Older Hypertensive Osteoarthritis Patients," *Am J Ther 8*585-95, 2001.
Whelton et al., "Nonsteroidal Anti-Inflammatory Drugs: Effects on Kidney Function," *J Clin Pharmcol 31*:588-598, 1991.
Whiteman et al., "Protection Against Peroxynitrite-Dependent Tyrosine Nitration and $\alpha_1$-Antiproteinase Inactivation by Ascorbic Acid. A Comparison with other Biological Antioxidants," *Free Rad Res 25*(3):275-283, Sep. 1996.
Wilgus et al., "Inhibition of Ultraviolet Light B-Induced Cutaneous Inflammation by a Specific Cyclooxygenase-2 Inhibitor," *Adv Exp Med Biol 507*:85-92, 2002.
Wilgus et al., "Topical application of selective cyclooxygenase inhibitor suppresses UVB mediated cutaneous inflammation," *Prostaglandins & Other Lipid Mediators 62*(4):367-384, 2000.
Wollheim, "Approaches to rheumatoid arthritis in 2000," *Curr Opin Rheumatol 13*(3):193-201, 2001.
Xiaozhen et al., "Induction of PGE$_2$ Production of COX-2 Expression in Human Gingival Fibroblasts Stimulated with LPS," *Med J Wuhan Uni 23*(4):301-305, Oct. 2002. (with English Abstract).
Xie et al., "Mitogen-Inducible Prostaglandin G/H Synthase: A New Target for Nonsteroidal Antiinflammatory Drugs," *Drug Development Research 25*(4):249-265, 1992.
Yamahara et al., "Inhibitory effect of crude Chinese drugs on the denaturation of human γ-globulin induced by heat and copper (2+)," *Shoyakugaku Zasshi 35*(2):103-107, 1981.

(56) References Cited

OTHER PUBLICATIONS

Yang et al., "Effects of Green Tea Catechin on Phospholipase $A_2$ Activity and Antithrombus in Streptozotocin Diabetic Rats," *J Nutr Sci Vitaminol* 45:337-346, Jun. 1999.

Ye et al., "Anticancer Activity of *Scutellaria baicalensis* and its Potential Mechanism," *The Journal of Alternative and Complementary Medicine* 8(5):567-572, 2002.

Yoshida et al., "Thermogenic, anti-obesity effects of *bofu-tsusho-san* in MSG-obese mice," *International J Obesity* 19:717-722, 1995.

Yoshimura et al., "Vitamin E Prevents Increase in Oxidative Damage to Lipids and DNA in Liver of ODS Rats Given Total Body X-ray Irradiation," *Free Rad Res* 36(1):107-112, Jan. 2002.

You et al., "Cyclooxygenase/Lipoxygenase from Human Platelets by Polyhydroxylated/Methoxylated Flavonoids Isolated from Medicinal Plants," *Arch. Phar. Res.* 22(1):18-24, 1999.

Young et al., "The Mouse Ear Inflammatory Response to Topical Arachidonic Acid," *J Invest Dermatol* 82(4): 367-371, 1984.

Zhang et al., "Inhibition of Cancer Cell Proliferation and Prostaglandin $E_2$ Synthesis by *Scutellaria baicalensis*," *Cancer Research* 63:4037-4043, 2003.

Zhang et al., *China Journal of the Chinese Materia Medical* 27(4):254-257, 2002. (English translation provided).

Chen et al., "Medicine for preventing and treating eye disease comprises, e.g., *Chrysanthemum* flower, dandelion, *Forsythia* fruit, Ionicera flower, *Scutellaria* root, gentian root, *Andropogon* nardus, mullberry root bark and mint or bamboo leaf," WPI Accession No. 2003-355289, Apr. 1, 1998, 1 page.

Gupta, Third Party Submission, dated Feb. 15, 2013; received in USPTO Feb. 25, 2013, (3 pages).

Nakamura et al., "Effects of baicalin, baicalein, and wogonin on Interleukin-6 and Interleukin-8 expression, and nuclear factor-Kappab binding activities induced by Interleukin-1 beta in human retinal pigment epithelial cell line," *Exp. Eye Res.* 77(2):195-202, 2003. (2 pages). (Abstract only).

Xu et al., "[Stduy on flavonoids in Ligustrum Lucidum]," *Zhong Yao Cai* 30(5):538-540, May 2007, 1 page. (Abstract Only).

Zhang, "Specific medicine for treating common cold is made of the Chinese medicinal materials including *Bupleurum* root, white peony root, *Scutellaria* root, pinellia tuber, licorice, ginseng, fresh ginger, onicera flower, *Forsythia* fruit," WPI Accession No. 2000-673139, Sep. 13, 2000, 6 pages.

IDENTIFICATION OF FREE-B-RING FLAVONOIDS AS POTENT COX-2 INHIBITORS

CROSS-REFERENCE TO RELATED APPLICATIONS

This application is a continuation of U.S. patent application Ser. No. 13/493,820, filed Jun. 11, 2012 (now U.S. Pat. No. 8,535,735, issued Sep. 17, 2013); which is a continuation of U.S. patent application Ser. No. 13/084,419, filed Apr. 11, 2011 (now abandoned); which is a continuation of U.S. patent application Ser. No. 11/676,528, filed Feb. 20, 2007 (now U.S. Pat. No. 7,972,632); which is a continuation of U.S. patent application Ser. No. 10/469,275, filed Oct. 23, 2003 (now U.S. Pat. No. 7,192,611); which is a National Phase Application of International Application No. PCT/US2003/006098, filed Feb. 28, 2003 (now expired); which is a continuation of U.S. patent application Ser. No. 10/091,362, filed Mar. 1, 2002 (now abandoned). These applications are incorporated herein by reference in their entirety.

FIELD OF THE INVENTION

This invention relates generally to a method for the prevention and treatment of COX-2 mediated diseases and conditions. Specifically, the present invention relates to a method for the prevention and treatment of COX-2 mediated diseases and conditions by administration of compounds referred to herein as Free-B-Ring flavonoids. Included in this invention is an improved method to generate standardized Free-B-Ring flavonoid extracts from plant sources.

BACKGROUND OF THE INVENTION

The liberation and metabolism of arachidonic acid (AA) from the cell membrane, results in the generation of pro-inflammatory metabolites by several different pathways. Arguably, the two most important pathways to inflammation are mediated by the enzymes 5-lipoxygenase (5-LO) and cyclooxygenase (COX). These are parallel pathways that result in the generation of leukotrienes and prostaglandins, respectively, which play important roles in the initiation and progression of the inflammatory response. These vasoactive compounds are chemotaxins, which both promote infiltration of inflammatory cells into tissues and serve to prolong the inflammatory response. Consequently, the enzymes responsible for generating these mediators of inflammation have become the targets for many new anti-inflammatory drugs.

Inhibition of the enzyme cyclooxygenase (COX) is the mechanism of action attributed to most nonsteroidal anti-inflammatory drugs (NSAIDS). There are two distinct isoforms of the COX enzyme (COX-1 and COX-2) that share approximately 60% sequence homology, but differ in expression profiles and function. COX-1 is a constitutive form of the enzyme that has been linked to the production of physiologically important prostaglandins, which help regulate normal physiological functions, such as platelet aggregation, protection of cell function in the stomach and maintenance of normal kidney function. (Dannhardt and Kiefer (2001) Eur. J. Med. Chem. 36:109-26). The second isoform, COX-2, is a form of the enzyme that is inducible by pro-inflammatory cytokines, such as interleukin-1β(IL-1β) and other growth factors. (Herschmann (1994) Cancer Metastasis Rev. 134:241-56; Xie et al. (1992) Drugs Dev. Res. 25:249-65). This isoform catalyzes the production of prostaglandin E2 (PGE2) from arachidonic acid (AA). Inhibition of COX-2 is responsible for the anti-inflammatory activities of conventional NSAIDs.

Because the mechanism of action of COX-2 inhibitors overlaps with that of most conventional NSAID's, COX-2 inhibitors are used to treat many of the same symptoms, including pain and swelling associated with inflammation in transient conditions and chronic diseases in which inflammation plays a critical role. Transient conditions include treatment of inflammation associated with minor abrasions, sunburn or contact dermatitis, as well as, the relief of pain associated with tension and migraine headaches and menstrual cramps. Applications to chronic conditions include arthritic diseases, such as rheumatoid arthritis and osteoarthritis. Although, rheumatoid arthritis is largely an autoimmune disease and osteoarthritis is caused by the degradation of cartilage in joints, reducing the inflammation associated with each provides a significant increase in the quality of life for those suffering from these diseases. (Wienberg (2001) Immunol. Res. 22:319-41; Wollhiem (2000) Curr. Opin. Rheum. 13:193-201). In addition to rheumatoid arthritis, inflammation is a component of rheumatic diseases in general. Therefore, the use of COX inhibitors has been expanded to include diseases, such as systemic lupus erythromatosus (SLE) (Goebel et al. (1999) Chem. Res. Tox. 12:488-500; Patrono et al. (1985) J. Clin. Invest. 76:1011-1018), as well as, rheumatic skin conditions, such as scleroderma. COX inhibitors are also used for the relief of inflammatory skin conditions that are not of rheumatic origin, such as psoriasis, in which reducing the inflammation resulting from the over production of prostaglandins could provide a direct benefit. (Fogh et al. (1993) Acta Derm Venerologica 73:191-3). Simply stated COX inhibitors are useful for the treatment of symptoms of chronic inflammatory diseases, as well as, the occasional ache and pain resulting from transient inflammation.

In addition to their use as anti-inflammatory agents, another potential role for COX inhibitors is in the treatment of cancer. Over expression of COX-2 has been demonstrated in various human malignancies and inhibitors of COX-2 have been shown to be efficacious in the treatment of animals with skin, breast and bladder tumors. While the mechanism of action is not completely defined, the over expression of COX-2 has been shown to inhibit apoptosis and increase the invasiveness of tumorgenic cell types. (Dempke et al. (2001) J. Can. Res. Clin. Oncol. 127:411-17; Moore and Simmons (2000) Current Med. Chem. 7:1131-44). It is possible that enhanced production of prostaglandins resulting from the over expression of COX-2 promotes cellular proliferation and consequently, increases angiogenesis. (Moore and Simmons (2000) Current Med. Chem. 7:1131-44; Fenton et al. (2001) Am. J. Clin. Oncol. 24:453-57).

There have been a number of clinical studies evaluating COX-2 inhibitors for potential use in the prevention and treatment of different type of cancers. Aspirin, a non-specific NSAID, for example, has been found to reduce the incidence of colorectal cancer by 40-50% (Giovannucci et al. (1995) N Engl J. Med. 333:609-614) and mortality by 50% (Smalley et al. (1999) Arch Intern Med. 159:161-166). In 1999, the FDA approved the COX-2 inhibitor CeleCOXib for use in FAP (Familial Ademonatous Polyposis) to reduce colorectal cancer mortality. It is believed that other cancers, with evidence of COX-2 involvement, may be successfully prevented and/or treated with COX-2 inhibitors including, but not limited to esophageal cancer, head and neck cancer, breast cancer, bladder cancer, cervical cancer, prostate cancer, hepatocellular carcinoma and non-small cell lung cancer. (Jaeckel et al.

(2001) Arch. Otolarnygol. 127:1253-59; Kirschenbaum et al. (2001) Urology 58:127-31; Dannhardt and Kiefer (2001) Eur. J. Med. Chem. 36:109-26). COX-2 inhibitors may also prove successful in preventing colon cancer in high-risk patients. There is also evidence that COX-2 inhibitors can prevent or even reverse several types of life-threatening cancers. To date, as many as fifty studies show that COX-2 inhibitors can prevent premalignant and malignant tumors in animals, and possibly prevent bladder, esophageal and skin cancers as well.

Recent scientific progress has identified correlations between COX-2 expression, general inflammation and the pathogenesis of Alzheimer's Disease (AD). (Ho et al. (2001) Arch. Neurol. 58:487-92). In animal models, transgenic mice that over express the COX-2 enzyme have neurons that are more susceptible to damage. The National Institute on Aging (NIA) is launching a clinical trial to determine whether NSAIDs can slow the progression of Alzheimer's Disease. Naproxen (a non-selective NSAID) and rofeCOXib (Vioxx, a COX-2 specific selective NSAID) will be evaluated. Previous evidence has indicated inflammation contributes to Alzheimer's Disease. According to the Alzheimer's Association and the NIA, about 4 million people suffer from AD in the U.S.; and this is expected to increase to 14 million by mid-century.

The COX enzyme (also known as prostaglandin H2 synthase) catalyzes two separate reactions. In the first reaction, arachidonic acid is metabolized to form the unstable prostaglandin G2 (PGG2), a cyclooxygenase reaction. In the second reaction, PGG2 is converted to the endoperoxide PGH2, a peroxidase reaction. The short-lived PGH2 non-enzymatically degrades to PGE2. The compounds described herein are the result of a discovery strategy that combined an assay focused on the inhibition of COX-1 and COX-2 peroxidase activity with a chemical dereplication process to identify novel inhibitors of the COX enzymes.

Flavonoids are a widely distributed group of natural products. The intake of flavonoids has been demonstrated to be inversely related to the risk of incident dementia. The mechanism of action, while not known, has been speculated as being due to the anti-oxidative effects of flavonoids. (Commenges et al. (2000) Eur. J. Epidemiol 16:357-363). Polyphenol flavones induce programmed cell death, differentiation, and growth inhibition in transformed colonocytes by acting at the mRNA level on genes including COX-2, Nf kappaB and bcl-X(L). (Wenzel et al. (2000) Cancer Res. 60:3823-3831). It has been reported that the number of hydroxyl groups on the B ring is important in the suppression of COX-2 transcriptional activity. (Mutoh et al. (2000) Jnp. J. Cancer Res. 91:686-691).

Free-B-Ring flavones and flavonols are a specific class of flavonoids, which have no substituent groups on the aromatic B ring, as illustrated by the following general structure:

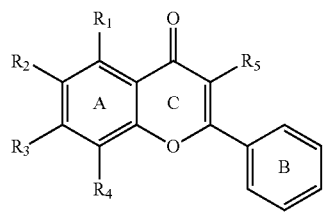

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

Free-B-Ring flavonoids are relatively rare. Out of a total 9396 flavonoids synthesized or isolated from natural sources, only 231 Free-B-Ring flavonoids are known. (The Combined Chemical Dictionary, Chapman & Hall/CRC, Version 5:1 Jun. 2001).

The Chinese medicinal plant, *Scutellaria baicalensis* contains significant amounts of Free-B-Ring flavonoids, including baicalein, baicalin, wogonin and baicalenoside. Traditionally, this plant has been used to treat a number of conditions including clearing away heat, purging fire, dampness-warm and summer fever syndromes; polydipsia resulting from high fever; carbuncle, sores and other pyogenic skin infections; upper respiratory infections, such as acute tonsillitis, laryngopharyngitis and scarlet fever; viral hepatitis; nephritis; pelvitis; dysentery; hematemesis and epistaxis. This plant has also traditionally been used to prevent miscarriage. (See Encyclopedia of Chinese Traditional Medicine, ShangHai Science and Technology Press, ShangHai, China, 1998). Clinically *Scutellaria* is now used to treat conditions such as pediatric pneumonia, pediatric bacterial diarrhea, viral hepatitis, acute gallbladder inflammation, hypertension, topical acute inflammation, resulting from cuts and surgery, bronchial asthma and upper respiratory infections (Encyclopedian of Chinese Traditional Medicine, ShangHai Science and Technology Press, ShangHai, China, 1998). The pharmacological efficacy of *Scutellaria* roots for treating bronchial asthma is reportedly related to the presence of Free-B-Ring flavonoids and their suppression of eotaxin associated recruitment of eosinophils. (Nakajima et al. (2001) Planta Med. 67(2):132-135).

Free-B-Ring flavonoids have been reported to have diverse biological activity. For example, galangin (3,5,7-trihydroxyflavone) acts as anti-oxidant and free radical scavenger and is believed to be a promising candidate for anti-genotoxicity and cancer chemoprevention. (Heo et al. (2001) Mutat. Res. 488(2):135-150). It is an inhibitor of tyrosinase monophenolase (Kubo et al. (2000) Bioorg. Med. Chem. 8(7):1749-1755), an inhibitor of rabbit heart carbonyl reductase (Imamura et al. (2000) J. Biochem. 127(4):653-658), has antimicrobial activity (Afolayan and Meyer (1997) Ethnopharmacol. 57(3):177-181) and antiviral activity (Meyer et al. (1997) J. Ethnopharmacol. 56(2):165-169). Baicalein and galangin, two other Free-B-Ring flavonoids, have antiproliferative activity against human breast cancer cells. (So et al. (1997) Cancer Lett. 112(2):127-133).

Typically, flavonoids have been tested for activity randomly based upon their availability. Occasionally, the requirement of substitution on the B-ring has been emphasized for specific biological activity, such as the B-ring substitution required for high affinity binding to p-glycoprotein (Boumendjel et al. (2001) Bioorg. Med. Chem. Lett. 11(1): 75-77); cardiotonic effect (Itoigawa et al. (1999) J. Ethnopharmacol. 65(3): 267-272), protective effect on endothelial cells against linoleic acid hydroperoxide-induced toxicity (Kaneko and Baba (1999) Biosci Biotechnol. Biochem 63(2): 323-328), COX-1 inhibitory activity (Wang (2000) Phytomedicine 7:15-19) and prostaglandin endoperoxide synthase (Kalkbrenner et al. (1992) Pharmacology 44(1):1-12). Only a few publications have mentioned the significance of the unsubstituted B ring of the Free-B-Ring flavonoids. One example, is the use of 2-phenyl flavones, which inhibit NAD (P)H quinone acceptor oxidoreductase, as potential anticoagulants. (Chen et al. (2001) Biochem. Pharmacol. 61(11): 1417-1427).

The reported mechanism of action related to the anti-inflammatory activity of various Free-B-Ring flavonoids has been controversial. The anti-inflammatory activity of the Free-B-Ring flavonoids, chrysin (Liang et al. (2001) FEBS Lett. 496(1):12-18), wogonin (Chi et al. (2001) Biochem. Pharmacol. 61:1195-1203) and halangin (Raso et al. (2001) Life Sci. 68(8):921-931), has been associated with the suppression of inducible cyclooxygenase and nitric oxide synthase via activation of peroxisome-proliferator activated receptor gamma and influence on degranulation and AA release. (Tordera et al. (1994) Z. Naturforsch [C] 49:235-240). It has been reported that oroxylin, baicalein and wogonin inhibit 12-lipoxygenase activity without affecting cyclooxygenase. (You et al. (1999) Arch. Pharm. Res. 22(1): 18-24). More recently, the anti-inflammatory activity of wogonin, baicalin and baicalein has been reported as occurring through inhibition of inducible nitric oxide synthase and COX-2 gene expression induced by nitric oxide inhibitors and lipopolysaccharide. (Chen et al. (2001) Biochem. Pharmacol. 61(11):1417-1427). It has also been reported that oroxylin acts via suppression of nuclear factor-kappa B activation. (Chen et al. (2001) Biochem. Pharmacol. 61(11): 1417-1427). Finally, wogonin reportedly inhibits inducible PGE2 production in macrophages. (Wakabayashi and Yasui (2000) Eur. J. Pharmacol. 406(3):477-481). Inhibition of the phosphorylation of mitrogen-activated protein kinase and inhibition of $Ca^{2+}$ ionophore A23187 induced prostaglandin E2 release by baicalein has been reported as the mechanism of anti-inflammatory activity of Scutellariae Radix. (Nakahata et al. (1999) Nippon Yakurigaku Zasshi, 114, Supp. 11:215P-219P; Nakahata et al. (1998) Am. J. Chin Med. 26:311-323). Baicalin from *Sculettaria baicalensis*, reportedly inhibits superantigenic staphylococcal exotoxins stimulated T-cell proliferation and production of IL-1β, interleukin 6 (IL-6), tumor necrosis factor-α (TNF-α), and interferon-γ (IFN-γ). (Krakauer et al. (2001) FEBS Lett. 500:52-55). Thus, the anti-inflammatory activity of baicalin has been associated with inhibiting the proinflammatory cytokines mediated signaling pathways activated by superantigens. However, it has also been proposed that the anti-inflammatory activity of baicalin is due to the binding of a variety of chemokines, which limits their biological activity. (Li et al. (2000) Immunopharmacology 49:295-306). Recently, the effects of baicalin on adhesion molecule expression induced by thrombin and thrombin receptor agonist peptide (Kimura et al. (2001) Planta Med. 67:331-334), as well as, the inhibition of mitogen-activated protein kinase cascade (MAPK) (Nakahata et al. (1999) Nippon Yakurigaku Zasshi, 114, Supp 11:215P-219P; Nakahata et al. (1998) Am. J. Chin Med. 26:311-323) have been reported. To date there have been no reports that link Free-B-Ring flavonoids with COX-2 inhibitory activity.

To date, a number of naturally occurring Free-B-Ring flavonoids have been commercialized for varying uses. For example, liposome formulations of *Scutellaria* extracts have been utilized for skin care (U.S. Pat. Nos. 5,643,598; 5,443, 983). Baicalin has been used for preventing cancer, due to its inhibitory effects on oncogenes (U.S. Pat. No. 6,290,995). Baicalin and other compounds have been used as antiviral, antibacterial and immunomodulating agents (U.S. Pat. No. 6,083,921) and as natural anti-oxidants (Poland Pub. No. 9,849,256). Chrysin has been used for its anxiety reducing properties (U.S. Pat. No. 5,756,538). Anti-inflammatory flavonoids are used for the control and treatment of anorectal and colonic diseases (U.S. Pat. No. 5,858,371), and inhibition of lipoxygenase (U.S. Pat. No. 6,217,875). Flavonoid esters constitute active ingredients for cosmetic compositions (U.S. Pat. No. 6,235,294).

Japanese Patent No. 63027435, describes the extraction, and enrichment of baicalein and Japanese Patent No. 61050921 describes the purification of baicalin.

SUMMARY OF THE INVENTION

The present invention includes methods that are effective in inhibiting the cyclooxygenase enzyme COX-2. The method for inhibiting the cyclooxygenase enzyme COX-2 is comprised of administering a composition comprising a Free-B-Ring flavonoid or a composition containing a mixture of Free-B-Ring flavonoids to a host in need thereof.

The present also includes methods for the prevention and treatment of COX-2 mediated diseases and conditions. The method for preventing and treating COX-2 mediated diseases and conditions is comprised of administering to a host in need thereof an effective amount of a composition comprising a Free-B-Ring flavonoid or a composition containing a mixture of Free-B-Ring flavonoids and a pharmaceutically acceptable carrier.

The Free-B-Ring flavonoids that can be used in accordance with the following include compounds illustrated by the following general structure:

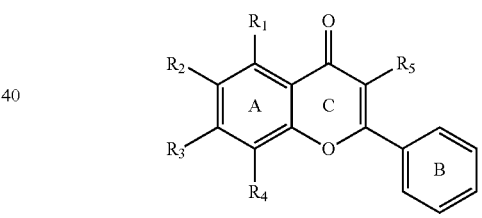

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methylaldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

The method of this invention can be used to treat and prevent a number of COX-2 mediated diseases and conditions including, but not limited to, osteoarthritis, rheumatoid arthritis, menstrual cramps, systemic lupus erythromatosus, psoriasis, chronic tension headaches, migraine headaches, topical wound and minor inflammatory conditions, inflammatory bowel disease and solid cancers.

The Free-B-Ring flavonoids of this invention may be obtained by synthetic methods or extracted from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus and Alpinia.*

The compositions of this invention can be administered by any method known to one of ordinary skill in the art. The modes of administration include, but are not limited to, enteral (oral) administration, parenteral (intravenous, subcutaneous, and intramuscular) administration and topical application. The method of treatment according to this invention comprises administering internally or topically to a patient in need thereof a therapeutically effective amount of the individual and/or a mixture of multiple Free-B-Ring flavonoids from a single source or multiple sources that include, but not limited to, synthetically obtained, naturally occurring, or any combination thereof.

This invention includes an improved method for isolating and purifying Free-B-Ring flavonoids from plants containing these compounds. The method of the present invention comprises: a) extracting the ground biomass of a plant containing Free-B-Ring flavonoids; b) neutralizing and concentrating said extract; and c) purifying said neutralized and concentrated extract. In a preferred embodiment of the invention the extract is purified using a method selected from the group consisting of recrystallization, precipitation, solvent partition and/or chromatographic separation. The present invention provides a commercially viable process for the isolation and purification of Free-B-Ring flavonoids having desirable physiological activity.

The present invention implements a strategy that combines a series of biomolecular screens with a chemical dereplication process to identify active plant extracts and the particular compounds within those extracts that specifically inhibit COX-2 enzymatic activity and inflammation. A total of 1230 plant extracts were screened for their ability to inhibit the peroxidase activity associated with recombinant COX-2. This primary screen identified 22 plant extracts that were further studied for their ability to specifically and selectively inhibit COX-2 in vitro in both cell based and whole blood assays. Those extracts that were efficacious in vitro were then tested for their ability to inhibit inflammation in vivo using a both air pouch and topical ear-swelling models of inflammation when administered by multiple routes (IP and oral). These studies resulted in the discovery of botanical extracts that inhibited COX-2 activity and were efficacious both in vitro and in vivo. These studies also resulted in the identification of specific Free-B-Ring flavonoids associated with COX-2 inhibition in each of these extracts. Applicant believes that this is first report of a correlation between Free-B-Ring flavonoid structure and COX-2 inhibitory activity.

It is to be understood that both the foregoing general description and the following detailed description are exemplary and explanatory only and are not restrictive of the invention as claimed.

DETAILED DESCRIPTION OF THE INVENTION

Figure 1:
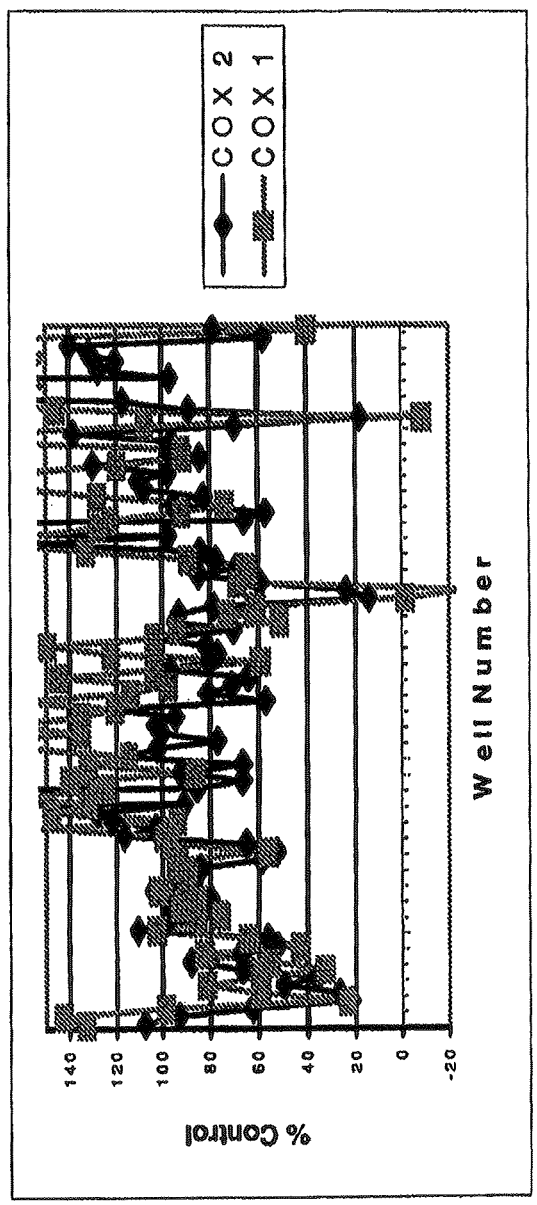
FIG. 1 depicts graphically the inhibition of COX-1 and COX-2 by HTP fractions from *Scutellaria baicaensis*. The extracts were prepared and fractionated as described in Examples 1 and 3. The extracts were examined for their inhibition of the peroxidase activity of recombinant ovine COX-1 (■) or ovine COX-2 (♦). The data is presented as percent of untreated control.

Various terms are used herein to refer to aspects of the present invention. To aid in the clarification of the description of the components of this invention, the following definitions are provided.

"Free-B-Ring Flavonoids" as used herein are a specific class of flavonoids, which have no substituent groups on the aromatic B ring, as illustrated by the following general structure:

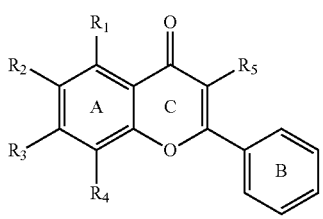

wherein $R_1$, $R_2$, $R_3$, $R_4$, and $R_5$ are independently selected from the group consisting of —H, —OH, —SH, OR, —SR, —NH$_2$, —NHR, —NR$_2$, —NR$_3^+$X$^-$, a carbon, oxygen, nitrogen or sulfur, glycoside of a single or a combination of multiple sugars including, but not limited to aldopentoses, methyl-aldopentose, aldohexoses, ketohexose and their chemical derivatives thereof;

wherein

R is an alkyl group having between 1-10 carbon atoms; and

X is selected from the group of pharmaceutically acceptable counter anions including, but not limited to hydroxyl, chloride, iodide, sulfate, phosphate, acetate, fluoride, carbonate, etc.

"Therapeutic" as used herein, includes treatment and/or prophylaxis. When used, therapeutic refers to humans, as well as, other animals.

"Pharmaceutically or therapeutically effective dose or amount" refers to a dosage level sufficient to induce a desired biological result. That result may be the alleviation of the signs, symptoms or causes of a disease or any other desirous alteration of a biological system.

A "host" is a living subject, human or animal, into which the compositions described herein are administered.

Note, that throughout this application various citations are provided. Each citation is specifically incorporated herein in its entirety by reference.

The present invention includes methods that are effective in inhibiting the cyclooxygenase enzyme COX-2. The method for inhibiting the cyclooxygenase enzyme COX-2 is comprised of administering a composition comprising a Free-B-Ring flavonoid or a composition containing a mixture of Free-B-Ring flavonoids to a host in need thereof.

The present also includes methods for the prevention and treatment of COX-2 mediated diseases and conditions. The method for preventing and treating COX-2 mediated diseases and conditions is comprised of administering to a host in need thereof an effective amount of a composition comprising a Free-B-Ring flavonoid or a composition containing a mixture of Free-B-Ring flavonoids and a pharmaceutically acceptable carrier.

The Free-B-Ring flavonoids that can be used in accordance with the following include compounds illustrated by the general structure set forth above. The Free-B-Ring flavonoids of this invention may be obtained by synthetic methods or may be isolated from the family of plants including, but not limited to Annonaceae, Asteraceae, Bignoniaceae, Combretaceae, Compositae, Euphorbiaceae, Labiatae, Lauranceae, Leguminosae, Moraceae, Pinaceae, Pteridaceae, Sinopteridaceae, Ulmaceae, and Zingiberacea. The Free-B-Ring flavonoids can be extracted, concentrated, and purified from the following genus of high plants, including but not limited to *Desmos, Achyrocline, Oroxylum, Buchenavia, Anaphalis, Cotula, Gnaphalium, Helichrysum, Centaurea, Eupatorium, Baccharis, Sapium, Scutellaria, Molsa, Colebrookea, Stachys, Origanum, Ziziphora, Lindera, Actinodaphne, Acacia, Derris, Glycyrrhiza, Millettia, Pongamia, Tephrosia, Artocarpus, Ficus, Pityrogramma, Notholaena, Pinus, Ulmus,* and *Alpinia*.

The flavonoids can be found in different parts of plants, including but not limited to stems, stem barks, twigs, tubers, roots, root barks, young shoots, seeds, rhizomes, flowers and other reproductive organs, leaves and other aerial parts.

In order to identify compounds able to inhibit the COX enzymes an extract library composed of 1230 extracts from 615 medicinal plants collected from China, India, and other countries was created. A general method for preparing the extracts is described in Example 1, which uses the *Scutellaria* species for purposes of illustration. The extraction process yields an organic and an aqueous extract for each species examined. The results of the extraction of various *Scutellaria* species are set forth in Table 1. These primary extracts are the source material used in the preliminary assay to identify inhibitors of the cyclooxygenase enzyme's peroxidase activity, which is one of the main functional activities of cyclooxygenase and is responsible for converting PGG2 to PGH2 and ultimately PGE2, as described in detail above.

This assay is described in Example 2 and the results are set forth in Table 2. With reference to Table 2, it can be seen that two species of *Scutellaria* and three other plant species, all of which contain Free-B-ring flavonoids as common components, showed inhibitory activity in the primary screen against the peroxidase activity of COX-2 albeit to differing degrees. The COX-2 inhibitory activity is found predominantly in the organic extracts, which contain the most of medium polarity Free-B-Ring flavonoids.

The COX-2 inhibitory activity from the primary assay of the crude extracts has been confirmed by measurement of dose response and IC$_{50}$ (the concentration required to inhibit 50% of the enzyme's activity). The IC$_{50}$ values are set forth in Table 3. As can be seen in Table 3, in this assay *Scutellaria orthocalyx* root extract and *Murica nana* leaf extract were the most efficacious (IC$_{50}$=6-10 mg/mL). Extracts from *Scutellaria* sp. that demonstrated the greatest selectivity against COX-2 were *Scutellaria lateriflora* (COX-2 IC$_{50}$: 30 mg/mL; COX-1 IC$_{50}$: 80 mg/mL). Thus, the primary screen for inhibitors of the COX enzyme identified five extracts containing Free-B-Ring flavonoids that were efficacious in vitro and some of which demonstrated specificity for the COX-2 enzyme.

In order to efficiently identify active compounds from plant extracts, a high throughput fractionation process was used, as described in Example 3. Briefly, the active organic and aqueous extracts were fractionated using two different methodologies, respectively. The fractions were collected in a 96 deep well plate. Each of the fractions was tested for its ability to inhibit COX activity as per the primary assay, as described in Example 4. The results are set forth in FIG. 1, which depicts the profile of COX-1 and COX-2 inhibition by various HTP fractions derived from the roots of *Scutellaria baicalensis*. As can be seen in FIG. 1, the most potent COX inhibitory activity was found in two major fractions, E11 and F11. It should be noted that three separate HTP fractions actually exhibit inhibitory activity, suggesting that there are multiple compounds contributing to the observed inhibitory effects of the whole extract.

The separation, purification and identification of the active Free-B-Ring flavonoids present in the organic extract of *Scutellaria orthocalyx* is described in Example 5. Using the methodology described in Example 5, baicalein was identified as the major active component in the organic extract from the roots of *Scutellaria orthocalyx*. As shown in the Example 6, several other Free-B-Ring flavonoids have been isolated and tested for inhibition of COX-1 and COX-2 enzymatic activity. The results are set forth in Table 4.

Example 7 and Table 5 set forth the content and quantity of the Free-B-Ring flavonoids in five active plant extracts from three different species of plants. The Free-B-Ring flavonoids are present in much greater amounts in the organic extracts verses the aqueous extracts. This explains why the COX-2 inhibitory activity has usually shown up in the organic extracts rather than the aqueous extracts.

The primary assay described in Example 2 to identify active extracts is a cell free system utilizing recombinant enzymes. To further demonstrate the biological activity of the active extracts and compounds, two models that represent cell based in vitro efficacy and animal based in vivo efficacy were employed. The method used to evaluate in vitro efficacy and selectivity is described in Example 8. Two cell lines were selected that could be induced to express primarily COX-1 (THP-1 cells) and COX-2 (HOSC cells), respectively. Each cell type was examined for the production of PGE2, the primary product of the COX enzymes. The results are set forth in Table 6, which shows that three organic extracts from three different species of Scutellaria showed inhibition of both the COX-1 and COX-2 enzymes with a preference for the COX-1 enzyme. While the use of the THP-1 cell line is important and demonstrates the ability of the active compounds to cross the cell membrane, it is an immortalized cell line, therefore evaluation of the efficacy of Free-B-Ring flavonoids based on a more relevant model system is desirable. As a result, the extracts were also evaluated using whole blood as the primary source of both COX-1 and COX-2 activity. This system measures the inhibition of the production of PGE2 vs. $TXB_2$ to differentiate between COX-2 and COX-1 inhibitory activity, respectively. The results, which are set forth in Table 6 demonstrate that both the COX-1 and COX-2 enzymes are inhibited by the Free-B-Ring flavonoids from all three Scutellaria root extracts. The $IC_{50}$ values suggest that within this system all Free-B-Ring flavonoids, except those from Scutellaria baicaensis are more efficacious against COX-2. Taken as a whole, the inhibitory effect of the active compounds within these extracts is significant and efficacious in both cell free and cell-based systems in vitro. Also, no cell toxicity been observed in the testing process.

Figure 3A:
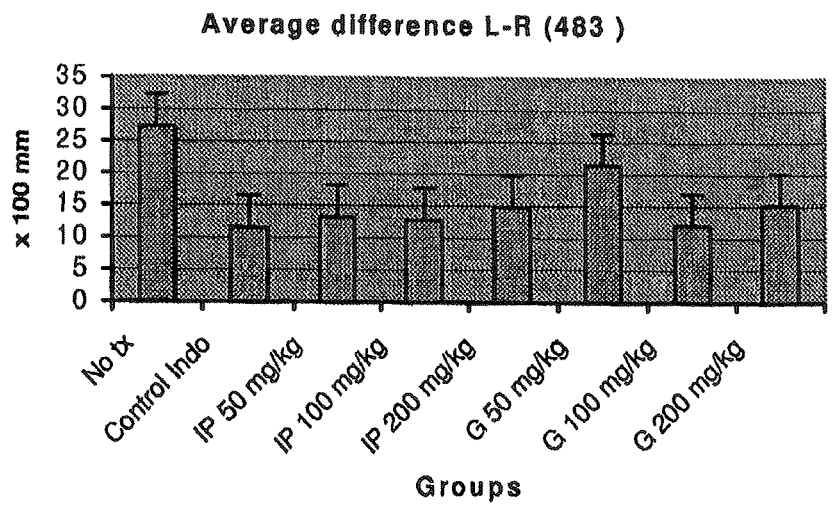
FIG. 3 demonstrates the in vivo efficacy of Free-B-Ring Flavonoids from *Scutellaria baicaensis* on arachidonic acid induced inflammation. The in vivo efficacy was evaluated based on the ability to inhibit swelling induced by direct application of arachidonic acid as described in Example 9. The average differences in swelling between the treated ears and control ears are represented in FIG. 3A.
FIG. 3B demonstrates the percent inhibition of each group in comparison to the arachidonic acid treated control.

Two separate in vivo models were employed to determine whether the in vitro efficacy observed from the Free-B-Ring flavonoids translated to an ability to inhibit in vivo inflammatory responses. The two models are described in Example 9. The first of these systems was designed to measure inflammation resulting directly from the arachidonic acid metabolism pathway. In this example, mice were treated with Free-B-Ring flavonoids from three Scutellaria species prior to the topical application of AA to the ear to induce the inflammatory response. The effect of pretreating the animals was then measured by the inhibition of the ear swelling using a micrometer. The Free-B-Ring flavonoids containing extracts from these three Scutellaria species demonstrated varying degrees of efficacy. For example, the Free-B-Ring flavonoids extracted from the roots of Scutellaria baicaensis inhibited ear swelling by 60% in comparison to controls when delivered by both oral and IP routes as illustrated in FIGS. 3A and B. This is the similar to the degree of inhibition seen with the positive control indomethacin, when delivered IP at a concentration of 5 mg/kg. Free-B-Ring flavonoids extracted from Scutellaria orthocalyx were efficacious when delivered by IP routes of administration, but had no effect when delivered by oral routes and finally the Free-B-Ring flavonoids extracted from Scutellaria lateriflora showed no effect regardless of the route of administration (data not shown).

The Free-B-Ring flavonoids isolated from Scutellaria baicaensis have been clearly demonstrated to be the most efficacious against inflammation induced directly by the arachidonic acid. Therefore, the efficacy of these Free-B-Ring flavonoids was examined using a second model in which multiple mechanisms of inflammation are ultimately responsible for the final effect. This system is therefore more relevant to naturally occurring inflammatory responses. Using this model, a very potent activator of the complement system is injected into an air pouch created on the back of Balb/C mice. This results in a cascade of inflammatory events including, infiltration of inflammatory cells, activation of COX enzymes, resulting in the release of $PGE_2$, the enzyme myeloperoxidase (MPO), and production of a very specific profile of pro-inflammatory cytokines including TNF-α. These studies demonstrated that even though the Free-B-Ring flavonoids isolated from Scutellaria baicaensis did not inhibit the initial infiltration (chemotactic response) of inflammatory cells into the air pouch, they blocked the activation of those cells. This is evidenced by the lack of MPO excreted into the extracellular fluid of the pouch and the noted lack of production of TNF-α. The results are set forth in FIG. 4. The data demonstrates that the Free-B-Ring flavonoids are efficacious and help control an inflammatory response in a model system where multiple inflammatory pathways are active.

The preparation of products for administration in pharmaceutical preparations may be performed by a variety of methods well known to those skilled in the art. The Free-B-Ring flavonoids may be formulated as an herb powder in the form of its natural existence; as solvent and/or supercritical fluid extracts in different concentrations; as enriched and purified compounds through recrystallization, column separation, solvent partition, precipitation and other means, as a pure and/or a mixture containing substantially purified Free-B-Ring flavonoids prepared by synthetic methods.

Various delivery systems are known in the art and can be used to administer the therapeutic compositions of the invention, e.g., aqueous solution, encapsulation in liposomes, microparticles, and microcapsules.

Therapeutic compositions of the invention may be administered parenterally by injection, although other effective administration forms, such as intraarticular injection, inhalant mists, orally active formulations, transdermal iontophoresis or suppositories are also envisioned. One preferred carrier is physiological saline solution, but it is contemplated that other pharmaceutically acceptable carriers may also be used. In one preferred embodiment, it is envisioned that the carrier and Free-B-Ring flavonoid(s) constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release or absorption of the ligand. Such excipients are those substances usually and customarily employed to formulate dosages for parental administration in either unit dose or multi-dose form.

Once the therapeutic composition has been formulated, it may be stored in sterile vials as a solution, suspension, gel, emulsion, solid, or dehydrated or lyophilized powder; or directly capsulated and/or tableted with other inert carriers for oral administration. Such formulations may be stored either in a ready to use form or requiring reconstitution immediately prior to administration. The manner of administering formulations containing the compositions for systemic delivery may be via enteral, subcutaneous, intramuscular, intravenous, intranasal or vaginal or rectal suppository.

The amount of the composition that will be effective in the treatment of a particular disorder or condition will depend on the nature of the disorder of condition, which can be determined by standard clinical techniques. In addition, in vitro or in vivo assays may optionally be employed to help identify optimal dosage ranges. The precise dose to be employed in the formulation will also depend on the route of administration, and the seriousness or advancement of the disease or condition, and should be decided according to the practitioner and each patient's circumstances. Effective doses may be extrapolated from dose-response curved derived from in vitro or animal model test systems. For example, an effective amount of the composition of the invention is readily determined by administering graded doses of the composition of the invention and observing the desired effect.

The method of treatment according to this invention comprises administering internally or topically to a patient in need thereof a therapeutically effective amount of the individual and/or a mixture of multiple Free-B-Ring flavonoids from a single source or multiple sources. The purity of the individual and/or a mixture of multiple Free-B-Ring flavonoids includes, but is not limited to 0.01% to 100%, depending on the methodology used to obtain the compound(s). In a preferred embodiment doses of the Free-B-Ring flavonoids and pharmaceutical compositions containing that same are an efficacious, nontoxic quantity generally selected from the range of 0.01 to 200 mg/kg of body weight. Persons skilled in the art using routine clinical testing are able to determine optimum doses for the particular ailment being treated.

This invention includes an improved method for isolating and purifying Free-B-Ring flavonoids from plants, which is described in Example 10. In Example 10, Free-B-Ring flavonoids from two *Scutellaria* species were extracted with different solvent systems. The results are set forth in Tables 7 and 8. The improved method of this invention comprises: extraction of the ground biomass of a plant containing Free-B-Ring flavonoids with single or combination of organic solvent and/or water; neutralization and concentration of the neutralized extract; and purification of said extract by recrystallization and/or chromatography. As provided above, these Free-B-Ring flavonoids can be isolated from the genera of more than twenty plant families. The method of this invention can be extended to the isolation of these compounds from any plant source containing these compounds.

Additionally the Free-B-Ring flavonoids can be isolated from various parts of the plant including, but not limited to, the whole plant, stems, stem bark, twigs, tubers, flowers, fruit, roots, root barks, young shoots, seeds, rhizomes and aerial parts. In a preferred embodiment the Free-B-Ring flavonoids are isolated from the roots, reproductive organs or the whole plant.

The solvent used for extraction of the ground biomass of the plant includes, but is not limited to water, acidified water, water in combination with miscible hydroxylated organic solvent(s) including, but not limited to, methanol or ethanol and an mixture of alcohols with other organic solvent(s) such as THF, acetone, ethyl acetate etc. In one embodiment the extract is neutralized to a pH of 4.5-5.5 and then concentrated and dried to yield a powder. The Free-B-Ring flavonoids can then be purified by various methods including, but not limited to recrystallization, solvent partition, precipitation, sublimation, and/or chromatographic methods including, but not limited to, ion exchange chromatography, absorption chromatography, reverse phase chromatography, size exclusive chromatography, ultra-filtration or a combination of thereof.

Example 11 describes a clinical study performed to evaluate the efficacy of free-B-ring flavonoids on the relief of pain caused by rheumatoid arthritis or osteoarthritis of the knee and/or hip. The study was a single-center, randomized, double-blind, placebo-controlled study. Sixty subjects (n=60) with rheumatoid arthritis or osteoarthritis of the knee and/or hip were randomly placed into four groups and treated for 60 days with a placebo, Univestin (250 mg/day or 500 mg/day) or Celebrex (200 mg/day). The Univestin consisted of a proprietary ratio of standardized extract of *Scutellaria baicalensis* Georgi with a Baicalin content of 62.5% (w/w) and total Free-B-Ring Flavonoids>75% (w/w). Celebrex is a trade name for a prescription drug that is a COX-2 selective inhibitor. Table 9 sets forth the WOMAC index scores before treatment (baseline scores) and Table 10 sets forth the changes in WOMAC index scores after treatment. FIGS. 5 to 8 illustrate the results of the study graphically.

As shown in the FIGS. 5 to 8, the WOMAC composite scores and individual subscores, related to pain, stiffness and physical function exhibited significant improvements after administration of free-B-ring flavonoids compared to the placebo group. Further, free-B-ring flavonoids exhibited the same effectiveness on pain relieve and improvement of physical function as the prescription drug Celebrex. Finally no difference in effectiveness was observed for the free-B-ring flavonoids at the two different dosages administered.

The following examples are provided for illustrative purposes only and are not intended to limit the scope of the invention.

EXAMPLES

Example 1

Preparation of Organic and Aqueous Extracts from *Scutellaria* Plants

Plant material from *Scutellaria orthocalyx* roots, *Scutellaria baicaensis* roots or *Scutellaria lateriflora* whole plant was ground to a particle size of no larger than 2 mm. Dried ground plant material (60 g) was then transferred to an Erlenmeyer flask and methanol:dichloromethane (1:1) (600 mL) was added. The mixture was shaken for one hour, filtered and the biomass was extracted again with methanol:dichloromethane (1:1) (600 mL). The organic extracts were combined and evaporated under vacuum to provide the organic extract (see Table 1 below). After organic extraction, the biomass was air dried and extracted once with ultra pure water (600 mL). The aqueous solution was filtered and freeze-dried to provide the aqueous extract (see Table 1 below).

TABLE 1

Yield of Organic and Aqueous Extracts of various *Scutellaria* species

| Plant Source | Amount | Organic Extract | Aqueous Extract |
|---|---|---|---|
| *Scutellaria orthocalyx* roots | 60 g | 4.04 g | 8.95 g |
| *Scutellaria baicaensis* roots | 60 g | 9.18 g | 7.18 g |
| *Scutellaria lateriflora* (whole plant) | 60 g | 6.54 g | 4.08 g |

Example 2

Inhibition of COX-2 and COX-1 Peroxidase Activity by Plant Extracts from Various *Scutellaria* Species The bioassay directed screening process for the identification of specific COX-2 inhibitors was designed to assay the peroxidase activity of the enzyme as described below.

Peroxidase Assay.

The assay to detect inhibitors of COX-2 was modified for a high throughput platform (Raz). Briefly, recombinant ovine COX-2 (Cayman) in peroxidase buffer (100 mM, TBS, 5 mM EDTA, 1 µM Heme, 0.01 mg epinephrine, 0.094% phenol) was incubated with extract (1:500 dilution) for 15 minutes. Quantablu (Pierce) substrate was added and allowed to develop for 45 minutes at 25° C. Luminescence was then read using a Wallac Victor 2 plate reader. The results are set forth in Table 2.

Table 2 sets forth the inhibition of enzyme by the organic and aqueous extracts obtained from five plant species, including the roots of two *Scutellaria* species and extracts from three other plant species, which are comprised of structurally similar Free-B-Ring Flavonoids. Data is presented as the percent of peroxidase activity relative to the recombinant ovine COX-2 enzyme and substrate alone. The percent inhibition by the organic extract ranged from 30% to 90%.

TABLE 2

Inhibition of COX-2 Peroxidase activity by *Scutellaria* species

| Plant Source | Inhibition of COX-2 by organic extract | Inhibition of COX-2 by aqueous extract |
| --- | --- | --- |
| *Scutellaria orthocalyx* (root) | 55% | 77% |
| *Scutellaria baicaensis* (root) | 75% | 0% |
| *Desmodium sambuense* (whole plant) | 55% | 39% |
| *Eucaluptus globulus* (leaf) | 30% | 10% |
| *Murica nana* (leaf) | 90% | 0% |

Comparison of the relative inhibition of the COX-1 and COX-2 isoforms requires the generation of $IC_{50}$ values for each of these enzymes. The $IC_{50}$ is defined as the concentration at which 50% inhibition of enzyme activity in relation to the control is achieved by a particular inhibitor. In the instant case, $IC_{50}$ values were found to range from 6 to 50 µg/mL and 7 to 80 µg/mL for the COX-2 and COX-1 enzymes, respectively, as set forth in Table 3. Comparison of the $IC_{50}$ values of COX-2 and COX-1 demonstrates the specificity of the organic extracts from various plants for each of these enzymes. The organic extract of *Scutellaria lateriflora* for example, shows preferential inhibition of COX-2 over COX-1 with $IC_{50}$ values of 30 and 80 µg/mL, respectively. While some extracts demonstrate preferential inhibition of COX-2, others do not. Examination of the HTP fractions and purified compounds from these fractions is necessary to determine the true specificity of inhibition for these extracts and compounds.

TABLE 3

$IC_{50}$ Values for Human and Ovine COX-2 and COX-1

| Plant Source | $IC_{50}$ Human COX-2 (µg/mL) | $IC_{50}$ Ovine COX-2 (µg/mL) | $IC_{50}$ Ovine COX-1 (µg/mL) |
| --- | --- | --- | --- |
| *Scutellaria orthocalyx* (root) | ND | 10 | 10 |
| *Scutellaria baicaensis* (root) | 30 | 20 | 20 |
| *Scutellaria lateriflora* (whole plant) | 20 | 30 | 80 |
| *Eucaluptus globulus* (leaf) | ND | 50 | 50 |
| *Murica nana* (leaf) | 5 | 6 | 7 |

Example 3

HTP Fractionation of Active Extracts

Organic extract (400 mg) from *Scutellaria baicaensis* roots was loaded onto a prepacked flash column. (2 cm ID×8.2 cm, 10 g silica gel). The column was eluted using a Hitachi high throughput purification (HTP) system with a gradient mobile phase of (A) 50:50 EtOAc:hexane and (B) methanol from 100% A to 100% B in 30 minutes at a flow rate of 5 mL/min. The separation was monitored using a broadband wavelength UV detector and the fractions were collected in a 96-deep-well plate at 1.9 mL/well using a Gilson fraction collector. The sample plate was dried under low vacuum and centrifugation. DMSO (1.5 mL) was used to dissolve the samples in each cell and a portion (100 µL was taken for the COX inhibition assay.

Aqueous extract (750 mg) from *Scutellaria baicaensis* roots was dissolved in water (5 mL), filtered through a 1 µm syringe filter and transferred to a 4 mL HPLC vial. The solution was then injected by an autosampler onto a prepacked reverse phase column (C-18, 15 µm particle size, 2.5 cm ID×10 cm with precolumn insert). The column was eluted using a Hitachi high throughput purification (HTP) system with a gradient mobile phase of (A) water and (B) methanol from 100% A to 100% B in 20 minutes, followed by 100% methanol for 5 minutes at a flow rate of 10 mL/min. The separation was monitored using a broadband wavelength UV detector and the fractions were collected in a 96-deep-well plate at 1.9 mL/well using a Gilson fraction collector. The sample plate was freeze-dried. Ultra pure water (1.5 mL) was used to dissolve samples in each cell and a portion of 100 µL was taken for the COX inhibition assay.

Example 4

Inhibition of COX Peroxidase Activity by HTP Fractions from Various *Scutellaria* Species Individual bioactive organic extracts were further characterized by examining each of the HTP fractions for the ability to inhibit the peroxidase activity of both COX-1 and COX-2 recombinant enzymes. The results are depicted in FIG. 1, which depicts the inhibition of COX-2 and COX-1 activity by HTP fractions from *Scutellaria baicaensis* isolated as described in Example 1 and 3. The profile depicted in FIG. 1 shows a peak of inhibition that is very selective for COX-2. Other *Scutellaria* sp. including *Scutellaria orthocalyx* and *Scutellaria lateriflora* demonstrate a similar peak of inhibition (data not shown). However, both the COX-1 and COX-2 enzymes demonstrate multiple peaks of inhibition suggesting that there is more than one molecule contributing to the initial inhibition profiles.

Example 5

Isolation and Purification of the Active Free-B-Ring Flavonoids from the Organic Extract of *Scutellaria orthocalyx*

The organic extract (5 g) from the roots of *Scutellaria orthocalyx*, isolated as described in Example 1, was loaded onto prepacked flash column (120 g silica, 40 μm particle size 32-60 μm, 25 cm×4 cm) and eluted with a gradient mobile phase of (A) 50:50 EtOAc:hexane and (B) methanol from 100% A to 100% B in 60 minutes at a flow rate of 15 mL/min. The fractions were collected in test tubes at 10 mL/fraction. The solvent was evaporated under vacuum and the sample in each fraction was dissolved in 1 mL of DMSO and an aliquot of 20 μL was transferred to a 96 well shallow dish plate and tested for COX inhibitory activity. Based on the COX assay results, active fractions #31 to #39 were combined and evaporated. Analysis by HPLC/PDA and LC/MS showed a major compound with a retention times of 8.9 minutes and a MS peak at 272 m/e. The product was further purified on a C18 semi-preparation column (25 cm×1 cm), with a gradient mobile phase of (A) water and (B) methanol, over a period of 45 minutes at a flow rate of 5 mL/minute. Eighty eight fractions were collected to yield 5.6 mg of light yellow solid. Purity was determined by HPLC/PDA and LC/MS, and comparison with standards and NMR data. $^1$H NMR: δ ppm. (DMSO-d6) 8.088 (2H, m, H-3',5'), 7.577 (3H, m, H-2',4',6'), 6.932 (1H, s, H-8), 6.613 (1H, s, H-3). MS: [M+1]+=271 m/e. The compound has been identified as Baicalein. The $IC_{50}$ of Baicalein against the COX-2 enzyme is 10 μg/mL.

Example 6

COX Inhibition of Purified Free-B-Ring Flavonoids

Several other Free-B-Ring Flavonoids have been obtained and tested at a concentration of 20 μg/mL for COX-2 inhibition activities using the methods described above. The results are summarized in Table 4.

TABLE 4

Inhibition of COX Enzymatic Activity by Purified Free-B-Ring Flavonoids

| Free-B-Ring Flavonoids | Inhibition of COX-1 | Inhibition of COX-2 |
|---|---|---|
| Baicalein | 107% | 109% |
| 5,6-Dihydroxy-7-methoxyflavone | 75% | 59% |
| 7,8-Dihydroxyflavone | 74% | 63% |
| Baicalin | 95% | 97% |
| Wogonin | 16% | 12% |

Example 7

Figure 2A:
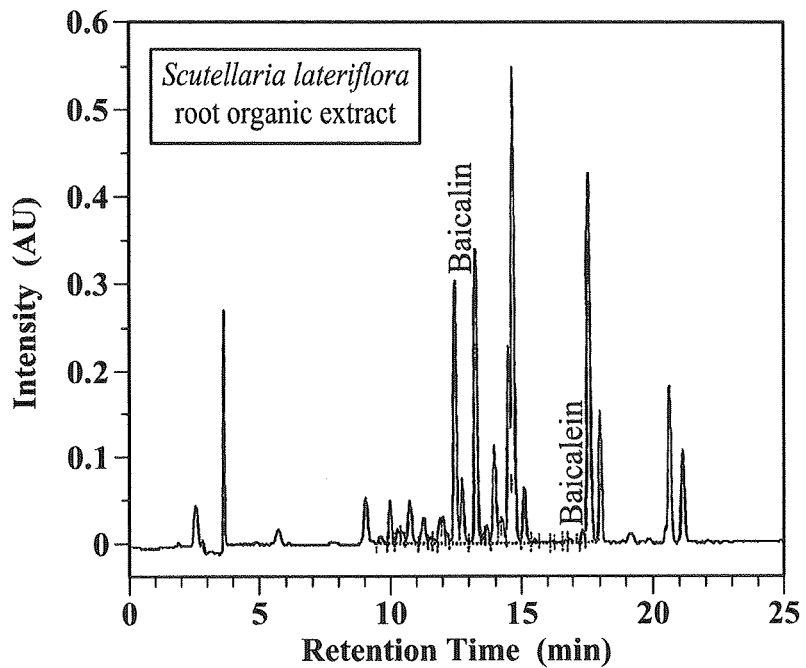
FIG. 2 depicts the high pressure liquid chromatography (HPLC) chromatograms of Free-B-Ring Flavonoids in organic extracts from *Scutellaria lateriflora* roots (FIG. 2A), *Scutellaria orthocalyx* roots (FIG. 2B) and *Scutellaria baicaensis* roots (FIG. 2C).
Figure 2B:
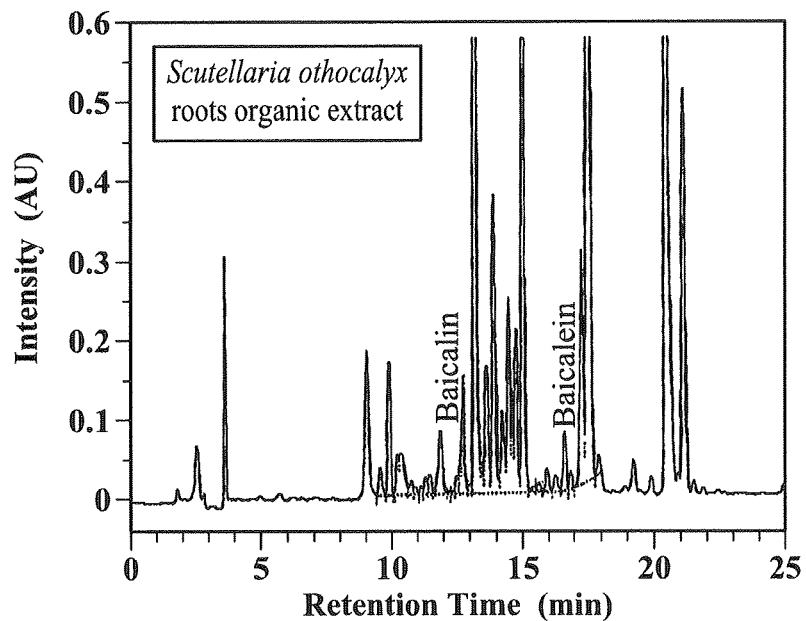
Figure 2C:
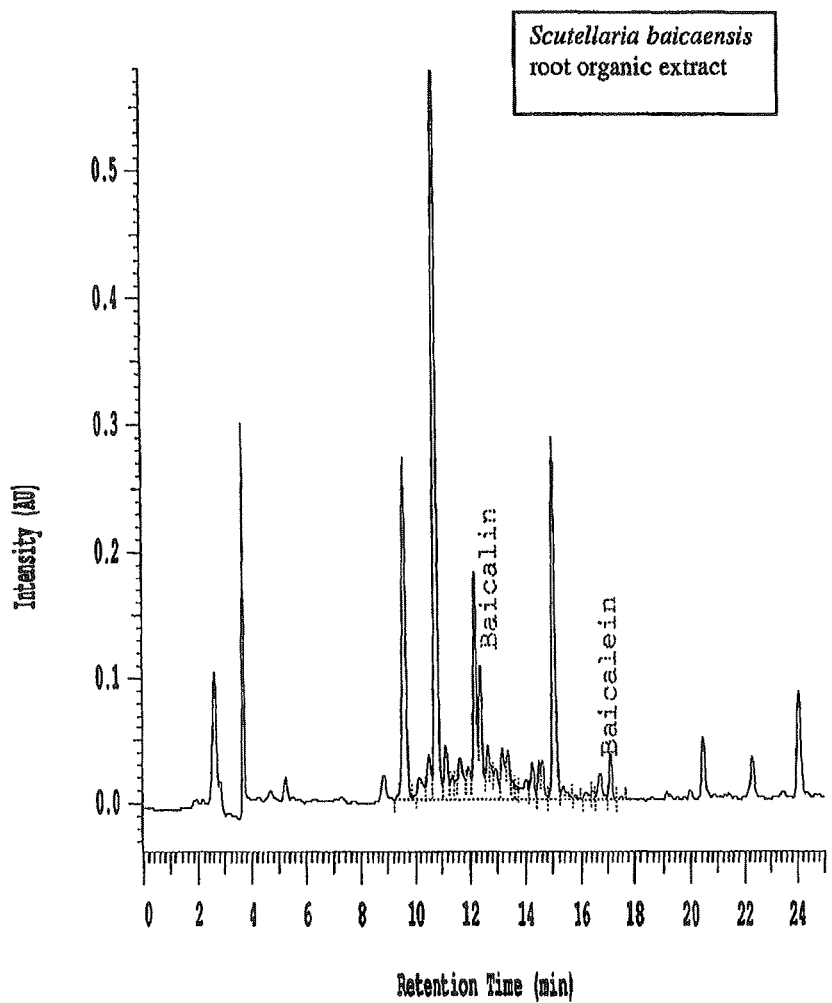

HPLC Quantification of Free-B-Ring Flavonoids in Active Extracts from *Scutellaria orthocalyx* Roots, *Scutellaria baicaensis* Roots and *Oroxylum indicum* Seeds The presence and quantity of Free-B-Ring Flavonoids in five active extracts from three different plant species have been confirmed and are set forth in the Table 5. The Free-B-Ring Flavonoids were quantitatively analyzed by HPLC using a Luna C-18 column (250×4.5 mm, 5 μm) using 0.1% phosphoric acid and acetonitrile gradient from 80% to 20% in 22 minutes. The Free-B-Ring Flavonoids were detected using a UV detector at 254 nm and identified based on retention time by comparison with Free-B-Ring Flavonoid standards. The HPLC chromatograms are depicted in FIG. 2.

TABLE 5

Free-B-Ring Flavonoid Content in Active Plant Extracts

| Active Extracts | Weight of Extract | % Extractible from BioMass | Total amount of Flavonoids | % Flavonoids in Extract |
|---|---|---|---|---|
| *Scutellaria orthocalyx* (AE)* | 8.95 g | 14.9% | 0.2 mg | 0.6% |
| *Scutellaria orthocalyx* (OE)* | 3.43 g | 5.7% | 1.95 mg | 6.4% |
| *Scutellaria baicaensis* (AE)* | 7.18 g | 12.0% | 0.03 mg | 0.07% |
| *Scutellaria baicaensis* (OE)* | 9.18 g | 15.3% | 20.3 mg | 35.5% |
| *Oroxylum indicum* (OE)* | 6.58 g | 11.0% | 0.4 mg | 2.2% |

*AE: Aqueous Extract
*OE: Organic Extract

Example 8

In Vitro Study of COX Inhibitory Activity of Free-B-Ring Flavonoids from Various *Scutellaria* Species In vitro efficacy and COX-2 specificity of Free-B-Ring Flavonoids isolated from various *Scutellaria* species were tested in cell based systems for their ability to inhibit the generation of arachidonic acid metabolites. Cell lines HOSC that constitutively express COX-2 and THP-1 that express COX-1 were tested for their ability to generate prostaglandin E2 (PGE2) in the presence of arachidonic acid.

COX-2 Cell Based Assay.

HOSC (ATCC#8304-CRL) cells were cultured to 80-90% confluence. The cells were trysinized, washed and resuspended in 10 mL at 1×10$^6$ cells/mL in tissue culture media (MEM). The cell suspension (200 pt) was plated out in 96 well tissue culture plates and incubated for 2 hours at 37° C. and 5% $CO_2$. The media was then replaced with new HOSC media containing 1 ng/mL IL-1b and incubated overnight. The media was removed again and replaced with 190 mL HOSC media. Test compounds were then added in 10 μL of HOSC media and were incubated for 15 minutes at 37° C. Arachidonic acid in HOSC media (20 mL, 100 μM) was added and the mixture was incubated for 10 minutes on a shaker at room temperature. Supernatant (20 μL) was transferred to new plates containing 190 μL/well of 100 μM indomethacin in ELISA buffer.

COX-1 Cell Based Assay.

THP-1 cells were suspended to a volume of 30 mL (5×10$^5$ cells/mL). TPA was added to a final concentration of 10 nM TPA and cultured for 48 hours to differentiate cells to macrophage (adherent). The cells were resuspended in HBSS (25 mL) and added to 96 well plates in 200 mL volume at 5×10$^5$ cells/well. The test compounds in RPMI 1640 (10 μL) were then added and incubated for 15 minutes at 37° C. Arachidonic acid in RPMI (20 μL) was then added and the mixture was incubated for 10 minutes on a shaker at room temperature. Supernatant (20 μL) was added to Elisa buffer (190 μL) containing indomethacin (100 μM). The supernatants were then analyzed by ELISA, as described below.

COX-2 Whole Blood Assay.

Peripheral blood from normal, healthy donors was collected by venipuncture. Whole blood (500 μL) was incubated with test compounds and extracts for 15 minutes at 37° C. Lipopolysaccharide (from *E. coli* serotype 0111:B4) was added to a final concentration of 100 μg/mL and cultured overnight at 37° C. Blood was centrifuged (12,000×g) and the plasma was collected. Plasma (100 μL) was added to methanol (400 μL) to precipitate proteins. Supernatants were measured for PGE2 production by ELISA. This procedure is a modification of the methods described by Brideau et al. (1996) Inflamm. Res. 45:68-74.

COX-1 Whole Blood Assay.

Fresh blood was collected in tubes not containing anti-coagulants and immediately aliquoted into 500 μL aliquots in siliconized microcentrifuge tubes. Test samples were added, vortexed and allowed to clot for 1 hour at 37° C. Samples were then centrifuged (12,000×g) and the plasma was collected. The plasma (100 μL) was added to methanol (400 μL) to precipitate proteins. Supernatants were measured for TXB2 production by ELISA. This procedure is a modification of the methods described by Brideau et al. (1996) Inflamm. Res. 45:68-74.

ELISA Assays.

Immunolon-4 ELISA plates were coated with capture antibody 0.5-4 μg/mL in carbonate buffer (pH 9.2) overnight at 4° C. The plates were washed and incubated for 2 hours with blocking buffer (PBS+1% BSA) at room temperature. The plates were washed again and test sample (100 μL) was added and incubated for 1 hour at room temperature while shaking. Peroxidase conjugated secondary antibody was added in a 50 μL volume containing 0.5-4 mg/mL and incubated for 1 hour at room temperature while shaking. The plates were then washed three times and TMB substrate (100 μL) was added. The plates were allowed to develop for 30 minutes, after which the reaction was stopped by the addition of 1 M phosphoric acid (100 μL). The plates were then read at 450 nm using a Wallac Victor 2 plate reader.

Cytotoxicity.

Cellular cytotoxicity was assessed using a colorimetric kit (Oxford biochemical research) that measures the release of lactate dehydrogenase in damaged cells. Assays were completed according to manufacturers' directions. No cytotoxicity has been observed for any of the tested compounds.

The results of the assays are set forth in Table 6. The data is presented as $IC_{50}$ values for direct comparison. With reference to Table 6, $IC_{50}$ values are generally lower for COX-1 than COX-2. Whole blood was also measured for the differential inhibition of PGE2 generation (a measure of COX-2 in this system) or thromboxane B2 (TXB2) (a measure of COX-1 activation). Referring to Table 6, these studies clearly demonstrate specificity for COX-2 inhibition from the organic extracts in two of the three species tested. Possible reasons for this discrepancy are the fundamental differences between immortalized cell lines that constitutively express each of the enzymes and primary cells derived from whole blood that that are induced to express COX enzymes. Primary cells are the more relevant model to study the in vivo inflammation process.

TABLE 6

Inhibition of COX Activity in Whole Cell Systems

| Plant Source | Cell Line Based Assay | | Whole Blood Assay | |
|---|---|---|---|---|
| | $IC_{50}$ COX-2 | $IC_{50}$ COX-1 | $IC_{50}$ COX-2 | $IC_{50}$ COX-1 |
| *Scutellaria orthocalyx* (root) | 50 μg/mL | 18 μg/mL | 10 μg/mL | >50 μg/mL |
| *Scutellaria baicaensis* (root) | 82 μg/mL | 40 μg/mL | 20 μg/mL | 8 μg/mL |
| *Scutellaria lateriflora* (whole plant) | 60 μg/mL | 30 μg/mL | 8 μg/mL | 20 μg/mL |

Example 9

In Vivo Study of COX Inhibitory Activity of Free-B-Ring Flavonoids from Various *Scutellaria* Species In vivo inhibition of inflammation was measured using two model systems. The first system (ear swelling model) measures inflammation induced directly by arachidonic acid. This is an excellent measure of COX-2 inhibition, but does not measure any of the cellular events which would occur upstream of arachidonic acid liberation from cell membrane phospholipids by phospholipase A2 (PLA2). Therefore, to determine how inhibitors function in a more biologically relevant response the air pouch model was employed. This model utilizes a strong activator of complement to induce an inflammatory response that is characterized by a strong cellular infiltrate and inflammatory mediator production including cytokines as well as arachidonic acid metabolites.

Ear Swelling Model.

Figure 3B:
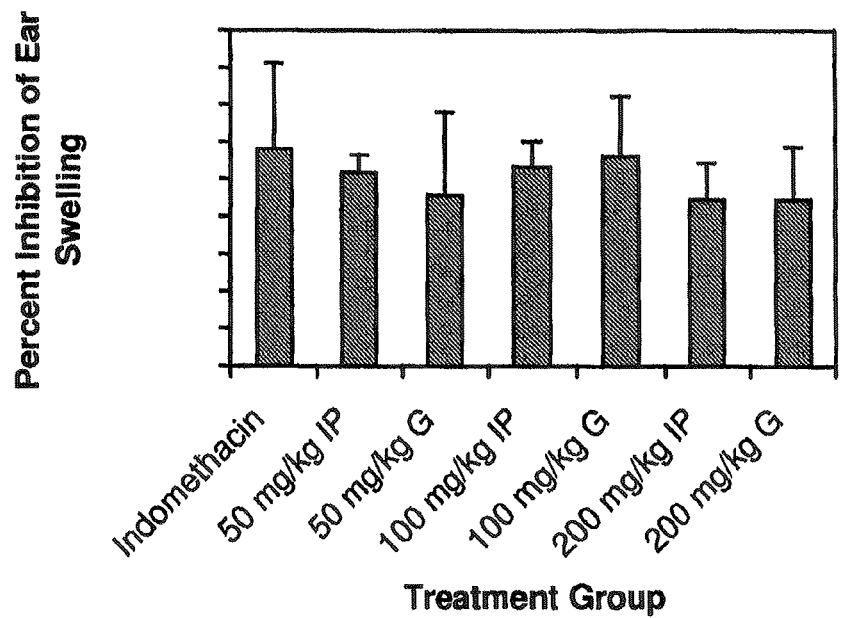

The ear swelling model is a direct measure of the inhibition of arachidonic acid metabolism. Arachidonic acid in acetone is applied topically to the ears of mice. The metabolism of arachidonic acid results in the production of proinflammatory mediators produced by the action of enzymes such as COX-2. Inhibition of the swelling is a direct measure of the inhibition of the enzymes involved in this pathway. The results are set forth in FIG. 3, which shows the effects of three extracts delivered either orally by gavage or interperitoneally (IP) at two time points (24 hours and 1 hour). Free-B-Ring Flavonoids isolated from *S. baicaensis* inhibited swelling when delivered by both IP and gavage although more efficacious by IP. (FIGS. 3A and B). Free-B-Ring Flavonoids isolated from *S. orthocalyx* inhibited the generation of these metabolites when given IP, but not orally, whereas extracts isolated from *S. lateriflora*, while being efficacious in vitro, had no effect in vivo (data not shown).

Air Pouch Model.

Because Free-B-Ring Flavonoids isolated from *S. baicaensis* were the more efficacious in the ear swelling model, they were also examined using the air pouch model of inflammation. Briefly, an air pouch was created on the back of the mice by injecting 3 mL of sterile air. The air pouch was maintained by additional injections of 1 mL of sterile air every other day for a period of one week. Animals were dosed using the same methods and concentrations described for the ear-swelling model and injected with Zymosan (into the air pouch) to initiate the inflammatory response. After four hours, the fluid within the pouch was collected and measured for the infiltration of inflammatory cells, myeloperoxidase (MPO) activity (a measure of cellular activation, degranulation), and tumor necrosis factor-α (TNF-α) production (a measure of activation). The results are set forth in FIG. 4.

Figure 4A:
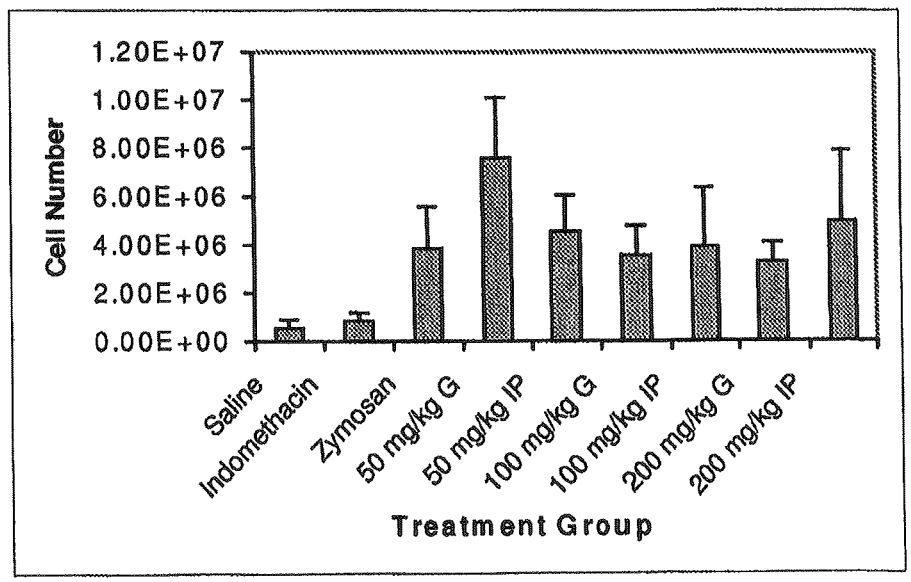
FIG. 4 illustrates the in vivo efficacy of Free-B-Ring Flavonoids isolated from *Scutellaria baicalensis* on inflammation induced by Zymosan. Zymosan was used to elicit a pro-inflammatory response in an air pouch as described in Example 9. Markers of inflammation including infiltration of pro-inflammatory cells (FIG. 4A), percent inhibition of MPO activity with in the air pouch fluid (FIG. 4B), and percent inhibition of TNF-α production (FIG. 4C) were used to evaluate the efficacy and mechanism of action of the anti-inflammatory activity of the Free-B-Ring Flavonoids from *Scutellaria baicalensis*.
Figure 4B:
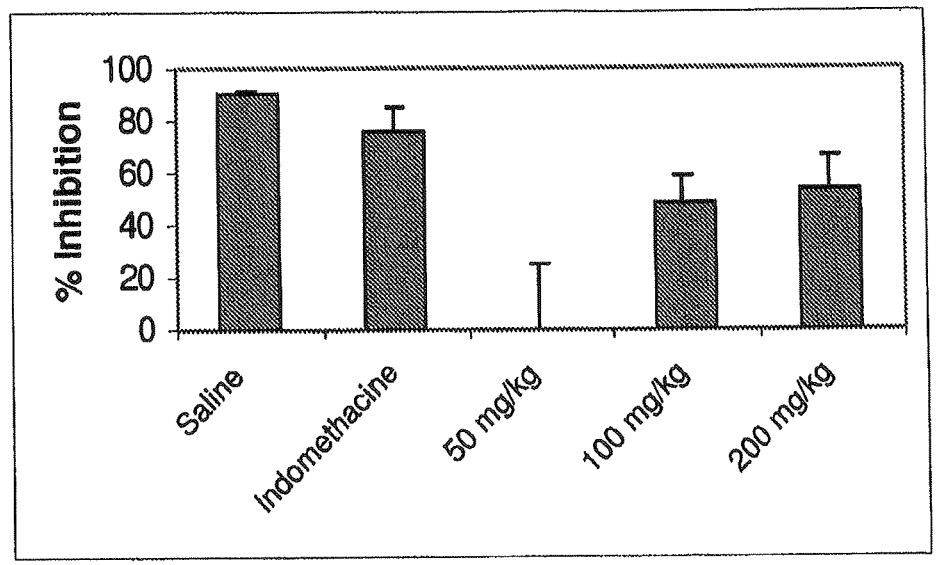
Figure 4C:
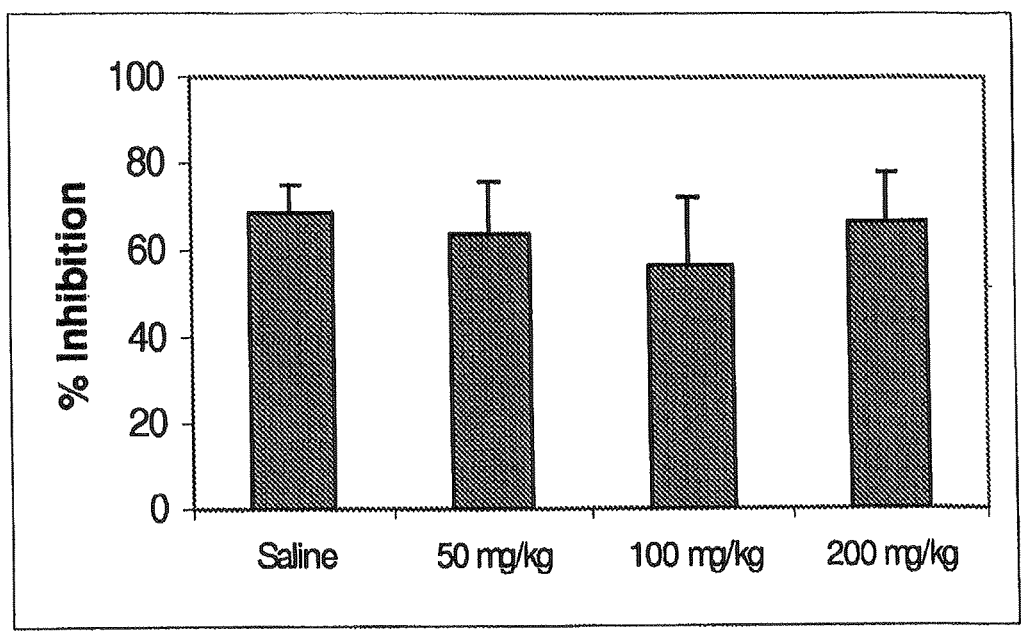
Figure 5:
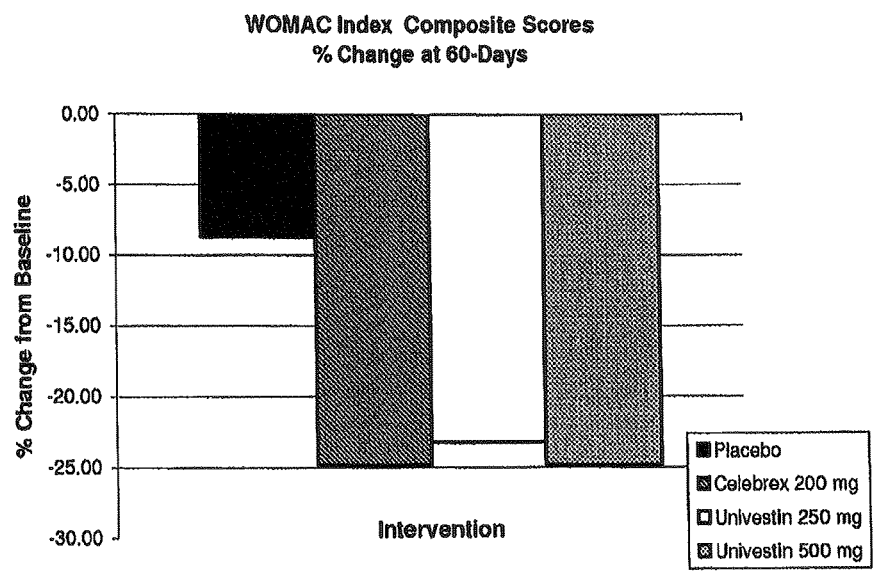
FIG. 5 illustrates graphically the % change in composite WOMAC index scores following 60 days of treatment with placebo, celebrex at a dosage of 200 mg/day, Univestin at a dosage of 250 mg/day and Univestin at a dosage of 500 mg/day as described in Example 11.
Figure 6:
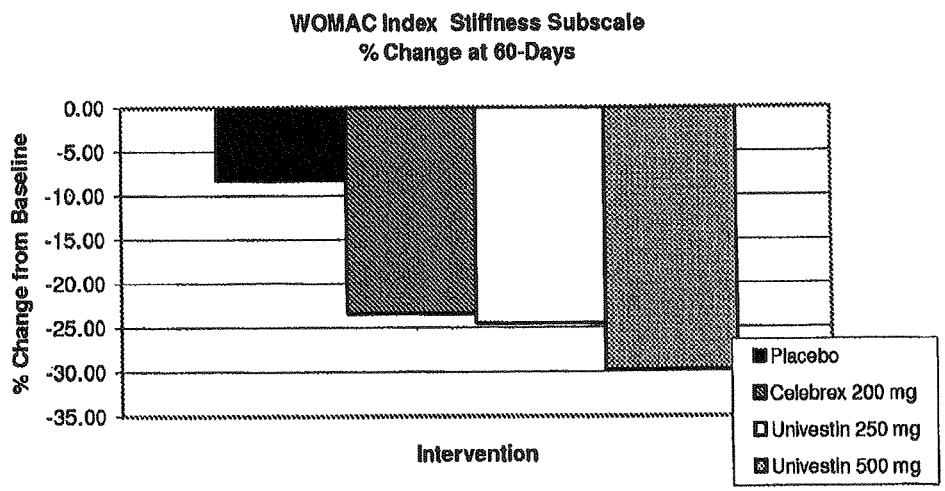
FIG. 6 illustrates graphically the % change in WOMAC index scores of stiffness following 60 days of treatment with placebo, celebrex at a dosage of 200 mg/day, Univestin at a dosage of 250 mg/day and Univestin at a dosage of 500 mg/day as described in Example 11.
Figure 7:
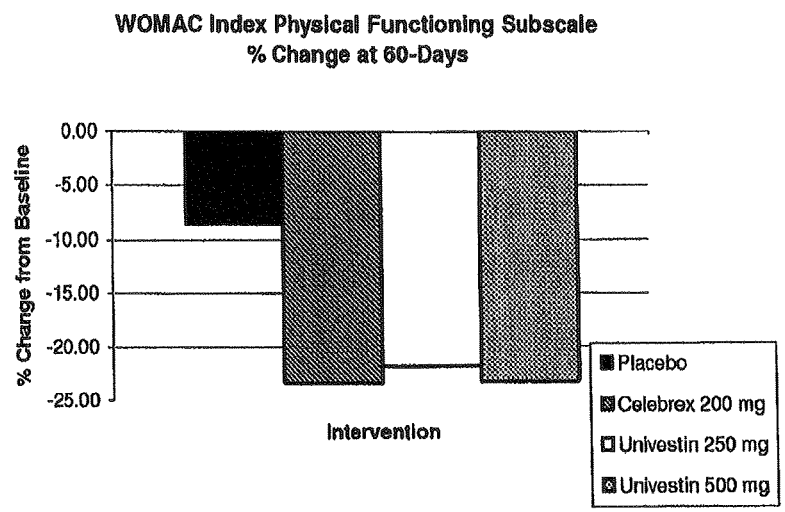
FIG. 7 illustrates graphically the % change in WOMAC index scores related to physical function following 60 days of treatment with placebo, celebrex at a dosage of 200 mg/day, Univestin at a dosage of 250 mg/day and Univestin at a dosage of 500 mg/day as described in Example 11.
Figure 8:
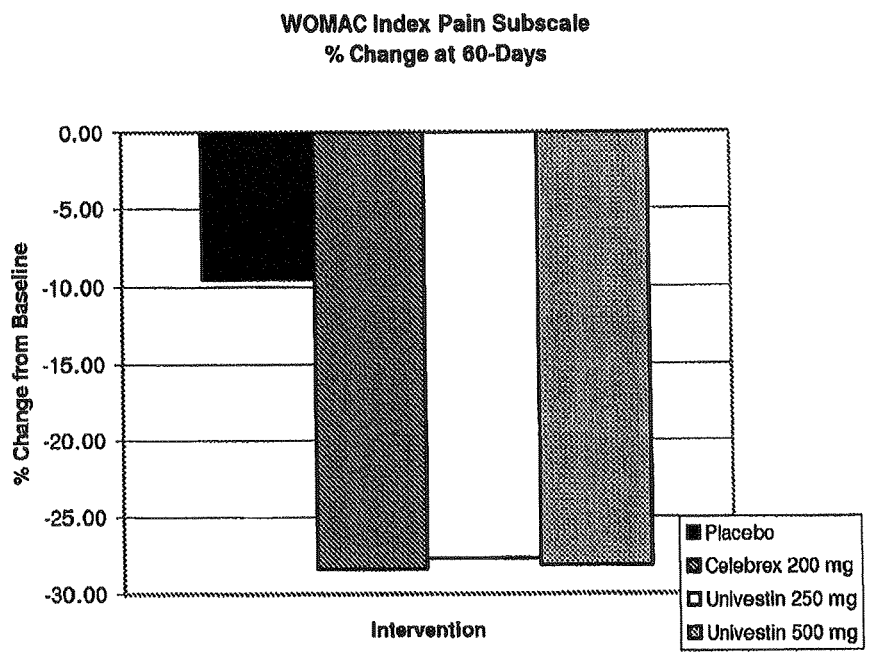
FIG. 8 illustrates graphically the % change in WOMAC index scores related to pain following 60 days of treatment with placebo, celebrex at a dosage of 200 mg/day, Univestin at a dosage of 250 mg/day and Univestin at a dosage of 500 mg/day as described in Example 11.

FIG. 4A shows the total number of cells collected from the air pouch fluid. While there was a strong response that was inhibited by controls (indomethacin), Free-B-Ring Flavonoids isolated from S. baicaensis did not inhibit the infiltration of the inflammatory cells (chemotaxis). Even though the chemotactic response was not diminished, the fluid was examined to determine whether the infiltrating cells have become activated by measuring MPO activity and TNF-α production. FIGS. 4B and 4C demonstrate that both MPO activity and TNF-α production are significantly reduced when the extract is administered IP, but not by gavages. These data suggest that although the Free-B-Ring Flavonoids do not inhibit the chemotactic response induced by complement activation they are still effective at reducing inflammation through the prevention of release and production of pro-inflammatory mediators.

Arachidonic Acid Induced Ear Swelling.

The ability of Free-B-Ring Flavonoids to directly inhibit inflammation in vivo was measured as previously described (Greenspan et al. (1999) J. Med. Chem. 42:164-172; Young et al. (1984) J. Invest. Dermat. 82:367-371). Briefly, groups of 5 Balb/C mice were given three dosages of test compounds as set forth in FIG. 4 either interperitoneally (I.P.) or orally by gavage, 24 hours and 1 hour prior to the application of arachidonic acid (AA). AA in acetone (2 mg/15 μL) was applied to the left ear, and acetone (15 pt) as a negative control was applied to the right ear. After 1 hour the animals were sacrificed by $CO_2$ inhalation and the thickness of the ears was measured using an engineer's micrometer. Controls included animals given AA, but not treated with anti-inflammatory agents, and animals treated with AA and indomethacin (I.P.) at 5 mg/kg.

Air Pouch Model of Inflammation.

Air pouch models were adapted from the methods of Rioja et al. (2000) Eur. J. Pharm. 397:207-217. Air pouches were established in groups of 5 Balb/C mice by injection of sterile air (3 mL) and maintained by additional injections of 1 mL every 2 days for a period of six days. Animals were given three dosages of test compounds as shown in FIG. 4 either I.P. or orally by gavage, 24 hours and 1 hour prior to the injection of 1% Zymosan (1 mL) into the pouch. After 4 hours, the animals were sacrificed by $CO_2$ inhalation and the air pouches were lavaged with sterile saline (3 mL). The lavage fluid was centrifuged and the total number of infiltrating cells determined. Supernatants were also retained and analyzed for myleoperoxidase (MPO) activity and the presence of TNF-α by ELISA as measures of activation.

Example 10

Development a Standardized Free-B-Ring Flavonoid Extract from Scutellaria Species Scutellaria orthocalyx (500 mg of ground root) was extracted twice with 25 mL of the following solvent systems. (1) 100% water, (2) 80:20 water:methanol, (3) 60:40 water:methanol, (4) 40:60 water:methanol, (5) 20:80 water:methanol, (6) 100% methanol, (7) 80:20 methanol:THF, (8) 60:40 methanol:THF. The extract solution was combined, concentrated and dried under low vacuum. Identification of chemical components was carried out by High Pressure Liquid Chromatography using a PhotoDiode Array detector (HPLC/PDA) and a 250 mm×4.6 mm C18 column. The chemical components were quantified based on retention time and PDA data using Baicalein, Baicalin, Scutellarein, and Wogonin standards. The results are set forth in Table 7.

TABLE 7

Quantification of Free-B-Ring Flavonoids Extracted from Scutellaria orthocalyx Using Different Solvent Systems

| Extraction Solvent | Weight of Extract | % Extractible from BioMass | Total amount of Flavonoids | % Flavonoids in Extract |
|---|---|---|---|---|
| 100% water | 96 mg | 19.2% | 0.02 mg | 0.20% |
| water:methanol (80:20) | 138.3 mg | 27.7% | 0.38 mg | 0.38% |
| water:methanol (60:40) | 169.5 mg | 33.9% | 0.78 mg | 8.39% |
| water:methanol (40:60) | 142.2 mg | 28.4% | 1.14 mg | 11.26% |
| water:methanol (20:80) | 104.5 mg | 20.9% | 0.94 mg | 7.99% |
| 100% methanol | 57.5 mg | 11.5% | 0.99 mg | 10.42% |
| methanol:THF (80:20) | 59.6 mg | 11.9% | 0.89 mg | 8.76% |
| methanol:THF (60:40) | 58.8 mg | 11.8% | 1.10 mg | 10.71% |

Scutellaria baicaensis (1000 mg of ground root) was extracted twice using 50 mL of a mixture of methanol and water as follows: (1) 100% water, (2) 70:30 water:methanol, (3) 50:50 water:methanol, (4) 30:70 water:methanol, (5) 100% methanol. The extract solution was combined, concentrated and dried under low vacuum. Identification of the chemical components was carried out by HPLC using a PhotoDiodeArray detector (HPLC/PDA), and a 250 mm×4.6 mm C18 column. The chemical components were quantified based on retention time and PDA data using Baicalein, Baicalin, Scutellarein, and Wogonin standards. The results are set forth in Table 8.

TABLE 8

Quantification of Free-B-Ring Flavonoids Extracted from Scutellaria baicaensis Using Different Solvent Systems

| Extraction Solvent | Weight of Extract | % Extractible from BioMass | Total amount of Flavonoids | % Flavonoids in Extract |
|---|---|---|---|---|
| 100% water | 277.5 mg | 27.8% | 0.01 mg | 0.09% |
| water:methanol (70:30) | 338.6 mg | 33.9% | 1.19 mg | 11.48% |
| water:methanol (50:50) | 304.3 mg | 30.4% | 1.99 mg | 18.93% |
| water:methanol (30:70) | 293.9 mg | 29.4% | 2.29 mg | 19.61% |
| 100% methanol | 204.2 mg | 20.4% | 2.73 mg | 24.51% |

Example 11

Clinical Evaluation of the Efficacy of Free-B-Ring Flavonoids on Pain Relieve of Rheumatoid Arthritis or Osteoarthritis of the Knee and/or Hip This clinical study was a single-center, randomized, double-blind, placebo-controlled study. Sixty subjects (n=60) with rheumatoid arthritis or osteoarthritis of the knee and/or hip were randomly placed into one of the following four groups:

| | | | | |
|---|---|---|---|---|
| A₀ | Placebo | n = 15 | Placebo | |
| A₁ | Dose 1 | n = 15 | Univestin | 250 mg/day (125 mg b.i.d.) |
| A₂ | Dose 2 | n = 15 | Univestin | 500 mg/day (250 mg b.i.d.) |
| A₃ | Active Control | n = 15 | Celebrex | 200 mg/day (100 mg b.i.d.) |

Univestin consists of a proprietary ratio of standardized extract of *Scutellaria baicalensis* Georgi with a Baicalin content of 62.5% (w/w) and total Free-B-Ring Flavonoids>75% (w/w). Celebrex is a trade name for a prescription drug that is a COX-2 selective inhibitor.

The subjects were sex-matched and recruited from the ages of 40 to 75. Treatment consisted of oral administration for 60 days of the placebo or active compound (Univestin or Celebrex) according to the above dose schedule. Subjects taking NSAIDs engaged in a two-week washout period before the beginning of the study. Physical activity was not restricted. Subjects were free to withdraw from the trial at any time for any reason. The efficacy of treatment was evaluated for 60 days after oral administration by physicians using the Western Ontario and McMaster Universities (WOMAC) Osteo-Arthritis Index. (See Lingard et al. (2001) The Journal of Bone & Joint Surgery 83(12):1856-1864; Soderman & Malchau (2000) Acta Orthop Scand. 71(1):39-46). This protocol was reviewed and approved by an IRB board from the University of Montreal. Table 9 sets forth the WOMAC index scores before treatment (baseline scores) and Table 10 sets forth the changes in WOMAC index scores after treatment for 60 days. FIGS. 5 to 8 illustrate the results of the study graphically.

What is claimed is:

1. A method for reducing joint dysfunction, comprising administering to a human or animal having joint pain, joint stiffness, or impaired physical function due to joint dysfunction a therapeutically effective amount of a composition comprising a *Scutellaria* extract enriched for a Free-B-Ring flavonoid or a mixture of Free-B-Ring flavonoids, wherein the method inhibits peroxidase activity which reduces joint dysfunction in the human or animal.

2. The method according to claim 1, the Free-B-Ring flavonoid or mixture of Free-B-Ring flavonoids are compounds having a structure as follows:

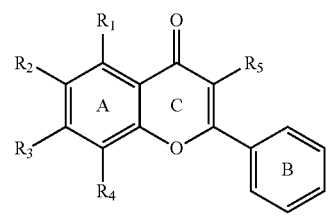

wherein $R_1$, $R_2$, $R_3$, $R_4$, and $R_5$ are independently a —H, —OH, —SH, —OR, —SR, —NH$_2$, —NHR, —N(R)$_2$, —N(R)$_3^+$X$^-$; a carbon, oxygen, nitrogen or sulfur glycoside of a single or a combination of multiple sugars selected from aldopentose, methyl-aldopentose, aldohexose, or ketohexose;

wherein R is an alkyl group having 1-10 carbon atoms; and X is hydroxyl, chloride, fluoride, iodide, sulfate, phosphate, acetate, or carbonate.

3. The method according to claim 1, wherein the *Scutellaria* is *Scutellaria baicalensis*, *Scutellariae lateriflora*, *Scutellariae radix*, or *Scutellariae orthocalyx*.

TABLE 9

WOMAC Scores at Baseline before Treatment
WOMAC SUBSCALE SCORES AT BASELINE

| WOMAC SUBSCALE | PLACEBO | | CELECOXIB | | UNIVESTIN 125 | | UNIVESTIN 250 | |
|---|---|---|---|---|---|---|---|---|
| | MEAN | SD | MEAN | SD | MEAN | SD | MEAN | SD |
| PAIN | 10.00 | 2.60 | 10.20 | 2.40 | 10.10 | 2.80 | 10.30 | 2.50 |
| STIFFNESS | 4.80 | 1.00 | 4.70 | 1.30 | 4.90 | 1.50 | 4.70 | 1.20 |
| PHYSICAL FUNTIONING | 38.00 | 9.50 | 37.00 | 9.90 | 37.50 | 100.00 | 36.50 | 1.00 |
| WOMAC COMPOSITE SCORES | 52.80 | 13.10 | 51.90 | 13.60 | 52.50 | 104.30 | 51.50 | 4.70 |

Patient BMI in all groups ranged from 31 to 33 ± 6.5.
No statistically significant difference among treatment groups was observed.

TABLE 10

WOMAC scores after 60 days of treatments

| WOMAC SUBSCALE | PLACEBO | | CELECOXIB | | UNIVESTIN 250 mg | | UNIVESTIN 500 mg | |
|---|---|---|---|---|---|---|---|---|
| | MEAN | % CHANGE | MEAN | % CHANGE | MEAN | % CHANGE | MEAN | % CHANGE |
| PAIN | −0.95 | −9.50 | −2.90 | −28.43 | −2.80 | −27.72 | −2.90 | −28.16 |
| STIFFNESS | −0.40 | −8.33 | −1.10 | −23.40 | −1.20 | −24.49 | −1.40 | −29.79 |
| PHYSICAL FUNTIONING | −3.25 | −8.55 | −8.90 | −24.05 | −8.20 | −21.87 | −8.50 | −23.29 |
| WOMAC COMPOSITE SCORES | −4.60 | −8.71 | −12.90 | −24.86 | −12.20 | −23.24 | −12.80 | −24.85 |

4. The method according to claim 1, wherein the *Scutellaria* extract enriched for a Free-B-Ring flavonoid or mixture of Free-B-Ring flavonoids is extracted from a plant part selected from stems, stem barks, twigs, tubers, roots, root barks, young shoots, seeds, rhizomes, flowers, leaves, or other aerial parts.

5. The method according to claim 1, wherein the joint dysfunction is associated with systemic lupus erythematosis, rheumatoid arthritis, or osteoarthritis.

6. The method according to claim 1, wherein the *Scutellaria* extract enriched for a Free-B-Ring flavonoid or mixture of Free-B-Ring flavonoids comprises baicalin.

7. The method according to claim 1, wherein the *Scutellaria* extract enriched for a Free-B-Ring flavonoid or mixture of Free-B-Ring flavonoids is formulated as a composition comprising a pharmaceutically acceptable carrier, excipient, or both.

8. The method according to claim 7, wherein the composition comprises 0.01% to 100% Free-B-Ring flavonoid or mixture of Free-B-Ring flavonoids.

9. The method according to claim 7, wherein the composition is administered at a dose of 0.01 to 200 mg/kg of body weight of the human or animal.

10. A method for reducing joint dysfunction, comprising administering to a human or animal having joint pain, joint stiffness, or impaired physical function due to joint dysfunction a therapeutically effective amount of a composition comprising an anti-oxidant enhancing *Scutellaria* extract enriched for a Free-B-Ring flavonoid or a mixture of Free-B-Ring flavonoids, wherein the method has anti-oxidant enhancing activity which inhibits peroxidase activity and reduces joint dysfunction in the human or animal.

11. The method according to claim 10, the Free-B-Ring flavonoid or mixture of Free-B-Ring flavonoids are compounds having a structure as follows:

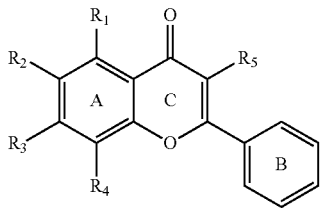

wherein $R_1$, $R_2$, $R_3$, $R_4$, and $R_5$ are independently a —H, —OH, —SH, —OR, —SR, —NH$_2$, —NHR, —N(R)$_2$, —N(R)$_3$$^+$X$^-$; a carbon, oxygen, nitrogen or sulfur glycoside of a single or a combination of multiple sugars selected from aldopentose, methyl-aldopentose, aldohexose, or ketohexose;

wherein R is an alkyl group having 1-10 carbon atoms; and

X is hydroxyl, chloride, fluoride, iodide, sulfate, phosphate, acetate, or carbonate.

12. The method according to claim 10, wherein the *Scutellaria* is *Scutellaria baicalensis, Scutellariae lateriflora, Scutellariae radix,* or *Scutellariae orthocalyx.*

13. The method according to claim 10, wherein the *Scutellaria* extract enriched for a Free-B-Ring flavonoid or mixture of Free-B-Ring flavonoids is extracted from a plant part selected from stems, stem barks, twigs, tubers, roots, root barks, young shoots, seeds, rhizomes, flowers, leaves, or other aerial parts.

14. The method according to claim 10, wherein the joint dysfunction is associated with systemic lupus erythematosis, rheumatoid arthritis, or osteoarthritis.

15. The method according to claim 10, wherein the human or animal has impaired physical function due to joint dysfunction.

16. The method according to claim 10, wherein the *Scutellaria* extract enriched for a Free-B-Ring flavonoid or mixture of Free-B-Ring flavonoids comprises baicalin.

17. The method according to claim 10, wherein the *Scutellaria* extract enriched for a Free-B-Ring flavonoid or mixture of Free-B-Ring flavonoids is formulated as a composition comprising a pharmaceutically acceptable carrier, excipient, or both.

18. The method according to claim 17, wherein the composition comprises 0.01% to 100% Free-B-Ring flavonoid or mixture of Free-B-Ring flavonoids.

19. The method according to claim 17, wherein the composition is administered at a dose of 0.01 to 200 mg/kg of body weight of the human or animal.

\* \* \* \* \*